United States Patent
Dobson et al.

(10) Patent No.: US 12,023,469 B2
(45) Date of Patent: Jul. 2, 2024

(54) INJECTION APPARATUS

(71) Applicant: Owen Mumford Limited, Woodstock (GB)

(72) Inventors: Matthew John Dobson, Woodstock (GB); Oliver Gould, Woodstock (GB); Andrew Hung, Woodstock (GB); Tahir Shabudin, Woodstock (GB); Matthew David Farmer, Woodstock (GB); Kuiwei Zhang, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 125 days.

(21) Appl. No.: 17/744,362

(22) Filed: May 13, 2022

(65) Prior Publication Data
US 2022/0273875 A1    Sep. 1, 2022

Related U.S. Application Data

(62) Division of application No. 16/494,074, filed as application No. PCT/GB2018/050673 on Mar. 15, 2018, now Pat. No. 11,376,364.

(30) Foreign Application Priority Data

Mar. 15, 2017  (GB) ..................... 1704136
Mar. 15, 2017  (GB) ..................... 1704137
(Continued)

(51) Int. Cl.
*A61M 5/20*      (2006.01)
*A61M 5/32*      (2006.01)

(52) U.S. Cl.
CPC ........ *A61M 5/2033* (2013.01); *A61M 5/3202* (2013.01); *A61M 5/3213* (2013.01);
(Continued)

(58) Field of Classification Search
CPC .............. A61M 5/3202; A61M 5/3213; A61M 5/3243; A61M 2005/2013; A61M 2005/208; A61M 2005/2073
See application file for complete search history.

(56) References Cited

U.S. PATENT DOCUMENTS 2,605,766 A    8/1952   Uytenbogaart
5,540,664 A    7/1996   Wyrick
(Continued)

FOREIGN PATENT DOCUMENTS

AU    1325995 A     7/1995
CN    101641125 A   2/2010
(Continued)

OTHER PUBLICATIONS

First Office Action from corresponding Chinese Patent Application No. 201880032612.5 dated Apr. 30, 2021 (17 pages) (English translation included).
(Continued)

*Primary Examiner* — Laura A Bouchelle
(74) *Attorney, Agent, or Firm* — Quarles & Brady LLP

(57) ABSTRACT

Disclosed is an auto-injection apparatus for receiving a syringe, including: an outer casing enclosing a drive assembly and a syringe carrier configured to hold a barrel of the syringe, the syringe carrier being forward of the drive assembly and having stowed and delivery positions; an interlock extending between the syringe carrier and a syringe carrier housing at least partially surrounding the syringe carrier, the interlock preventing forward motion of the syringe carrier under the influence of an insertion actuator whilst in the stowed position. The drive assembly includes the insertion actuator for inserting a needle of the syringe into an injection site and a delivery actuator for driving a plunger into a barrel of the syringe which contains a substance for injection. The syringe carrier includes an
(Continued)

interlock release mechanism which is configured to release the interlock such that the insertion actuator drives the syringe carrier forward.

16 Claims, 11 Drawing Sheets

(30) Foreign Application Priority Data

| Mar. 15, 2017 | (GB) | ................................... | 1704140 |
|---|---|---|---|
| Mar. 15, 2017 | (GB) | ................................... | 1704141 |
| Mar. 15, 2017 | (GB) | ................................... | 1704142 |
| Mar. 15, 2017 | (GB) | ................................... | 1704143 |

(52) U.S. Cl.
CPC ... *A61M 5/3271* (2013.01); *A61M 2005/2013* (2013.01); *A61M 2005/208* (2013.01)

(56) References Cited

U.S. PATENT DOCUMENTS

| 7,118,553 | B2 | 10/2006 | Scherer |
| 7,357,790 | B2 | 4/2008 | Hommann et al. |
| 8,409,138 | B2 | 4/2013 | James et al. |
| 8,864,718 | B2 * | 10/2014 | Karlsen ............... A61M 5/3202 604/197 |
| 9,011,387 | B2 | 4/2015 | Ekman et al. |
| 9,168,339 | B2 | 10/2015 | Cowe |
| 9,186,459 | B2 | 11/2015 | Bechmann et al. |
| 9,272,098 | B2 | 3/2016 | Hourmand et al. |
| 9,421,337 | B2 | 8/2016 | Kemp et al. |
| 9,636,467 | B2 | 5/2017 | Ekman et al. |
| 9,764,091 | B2 | 9/2017 | Bechmann et al. |
| 9,775,948 | B2 | 10/2017 | Bechmann et al. |
| 9,999,734 | B2 | 6/2018 | Cowe |
| 10,357,608 | B2 | 7/2019 | Bechmann et al. |
| 2008/0195056 | A1 | 8/2008 | Bishop et al. |
| 2010/0049125 | A1 | 2/2010 | James et al. |
| 2010/0262083 | A1 | 10/2010 | Grunhut et al. |
| 2013/0035645 | A1 | 2/2013 | Bicknell et al. |
| 2013/0102971 | A1 | 4/2013 | Olson |
| 2013/0131595 | A1 | 5/2013 | Ekman et al. |
| 2013/0317428 | A1 | 11/2013 | Brereton et al. |
| 2013/0324925 | A1 | 12/2013 | Brereton et al. |
| 2013/0324939 | A1 | 12/2013 | Brereton et al. |
| 2014/0276598 | A1 | 9/2014 | Markussen |
| 2015/0100031 | A1 | 4/2015 | Cowe |
| 2015/0367072 | A1 | 12/2015 | Constantineau et al. |
| 2016/0008540 | A1 | 1/2016 | Fourt et al. |
| 2016/0151586 | A1 | 6/2016 | Kemp |
| 2016/0193416 | A1 | 7/2016 | Olson et al. |
| 2016/0361502 | A1 | 12/2016 | Hommann et al. |
| 2017/0348487 | A1 | 12/2017 | Bechmann et al. |
| 2017/0348488 | A1 | 12/2017 | Bechmann et al. |
| 2018/0001025 | A1 | 1/2018 | Sarkinen et al. |
| 2018/0147352 | A1 | 5/2018 | Farmer et al. |
| 2018/0200442 | A1 | 7/2018 | Atterbury et al. |
| 2019/0030249 | A1 | 1/2019 | Gonzalez et al. |
| 2019/0143041 | A1 | 5/2019 | Gould |

FOREIGN PATENT DOCUMENTS

| CN | 101784297 A | 7/2010 |
| CN | 101790394 A | 7/2010 |
| CN | 102123753 A | 7/2011 |
| CN | 102665805 A | 9/2012 |
| CN | 102770173 A | 11/2012 |
| CN | 103476442 A | 12/2013 |
| CN | 103492000 A | 1/2014 |
| CN | 104902945 A | 9/2015 |
| CN | 105025957 A | 11/2015 |
| CN | 105492042 A | 4/2016 |
| CN | 106255522 A | 12/2016 |
| EP | 1790366 A1 | 5/2007 |
| EP | 2468334 A1 | 12/2010 |
| EP | 2468333 A1 | 6/2012 |
| EP | 2489380 A1 | 8/2012 |
| EP | 2823837 A1 | 1/2015 |
| FR | 2519866 A2 | 7/1983 |
| GB | 2488578 A | 9/2012 |
| GB | 2537638 A | 10/2016 |
| GB | 2541915 A | 3/2017 |
| WO | 9516481 A1 | 6/1995 |
| WO | 2005097238 A2 | 10/2005 |
| WO | 2006057604 A1 | 6/2006 |
| WO | 2008112472 A2 | 9/2008 |
| WO | 2009022132 A2 | 2/2009 |
| WO | 2010018411 A1 | 2/2010 |
| WO | 2011101375 A1 | 8/2011 |
| WO | 2011101381 A2 | 8/2011 |
| WO | 2011101383 A1 | 8/2011 |
| WO | 2012045833 A1 | 4/2012 |
| WO | 2012049484 A2 | 4/2012 |
| WO | 2012085580 A1 | 6/2012 |
| WO | 2012164389 A2 | 12/2012 |
| WO | 2013016832 A1 | 2/2013 |
| WO | 2013034984 A2 | 3/2013 |
| WO | 2014060563 A2 | 4/2014 |
| WO | 2015011488 A1 | 1/2015 |
| WO | 2015169608 A1 | 11/2015 |
| WO | 2016118688 A1 | 7/2016 |
| WO | 2016174245 A1 | 11/2016 |
| WO | 2016174249 A1 | 11/2016 |
| WO | 2016189286 A1 | 12/2016 |
| WO | 2017007850 A1 | 1/2017 |
| WO | 2017160626 A1 | 9/2017 |
| WO | 2017187140 A1 | 11/2017 |

OTHER PUBLICATIONS

First Office Action from corresponding Chinese Patent Application No. 201880032468.5 dated Mar. 29, 2021 (17 pages) (English translation included).
First Office Action from corresponding Chinese Patent Application No. 201880032544.2 dated Apr. 30, 2021 (14 Pages) (English translation included).
First Office Action from corresponding Chinese Patent Application No. 201880032470.2 dated Apr. 2, 2021 (15 pages) (English translation included).
International Search Report and Written Opinion, dated Jul. 9, 2018, from corresponding PCT application No. PCT/GB2018/050673.
Written Opinion of the International Preliminary Examining Authority, dated Mar. 8, 2019, from corresponding PCT Application No. PCT/GB2018/050673.
Combined Search and Examination Report, dated Aug. 15, 2017, from corresponding GB application No. 1704140.1.
Combined Search and Examination Report, dated Aug. 14, 2017, from corresponding GB application No. 1704143.5.
Combined Search and Examination Report, dated Aug. 15, 2017, from corresponding GB application No. 1704137.7.
Combined Search and Examination Report, dated Aug. 15, 2017, from corresponding GB application No. 1704136.9.
Combined Search and Examination Report, dated Aug. 14, 2017, from corresponding GB application No. 1704142.7.
Combined Search and Examination Report, dated Aug. 16, 2017, from corresponding GB application No. 1704141.9.
Preliminary Report on Patentability, dated Jul. 26, 2019, from corresponding PCT application No. PCT/GB2018/050673.
International Search Report and Written Opinion, dated Jul. 3, 2018, from corresponding PCT application No. PCT/GB2018/050659.
International Search Report and Written Opinion, dated Jul. 3, 2018, from corresponding PCT application No. PCT/GB2018/050660.
International Search Report and Written Opinion, dated Jul. 3, 2018, from corresponding PCT application No. PCT/GB2018/050662.
International Search Report and Written Opinion, dated Aug. 6, 2018, from corresponding PCT application No. PCT/GB2018/050663.

(56) References Cited

OTHER PUBLICATIONS

International Search Report and Written Opinion, dated Jul. 9, 2018, from corresponding PCT application No. PCT/GB2018/050664.
International Search Report and Written Opinion, dated Jul. 9, 2018, from corresponding PCT application No. PCT/GB2018/050665.
First Office Action from corresponding Chinese Patent Application No. 201880032551.2, dated Mar. 24, 2021 (11 pages) (English translation included).
First Office Action from corresponding Chinese Patent Application No. 201880032486.3, dated Mar. 26, 2021 (12 pages) (English translation included).

* cited by examiner

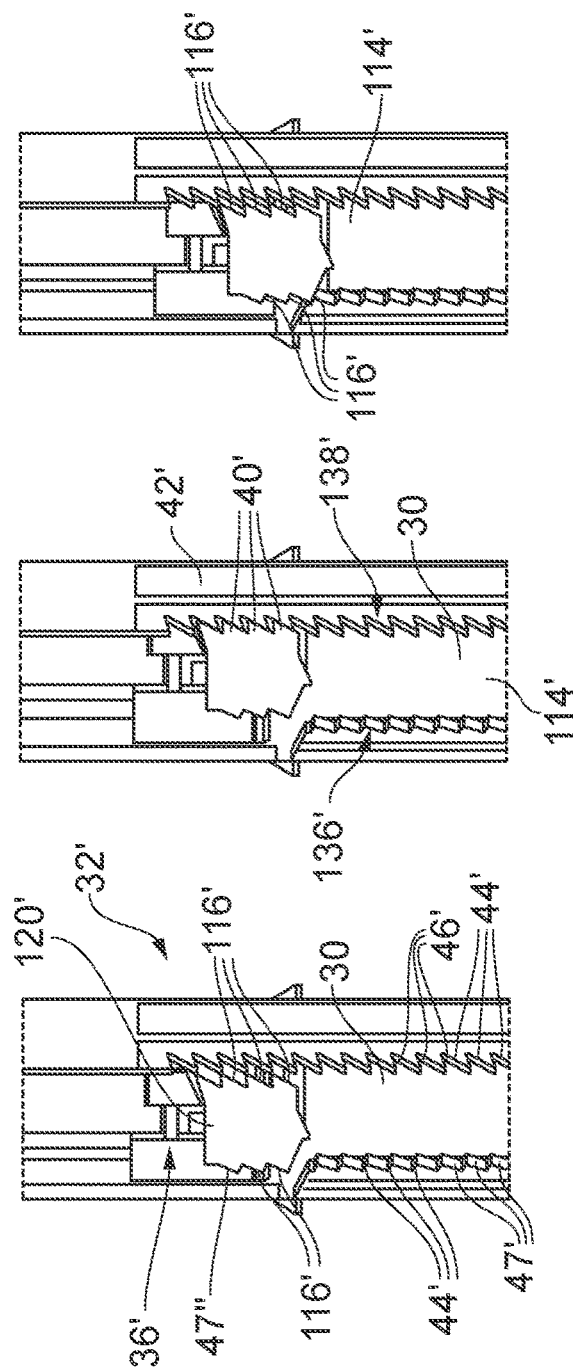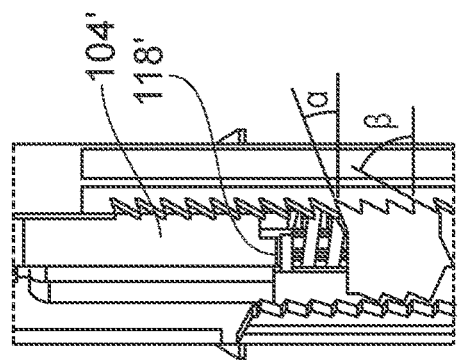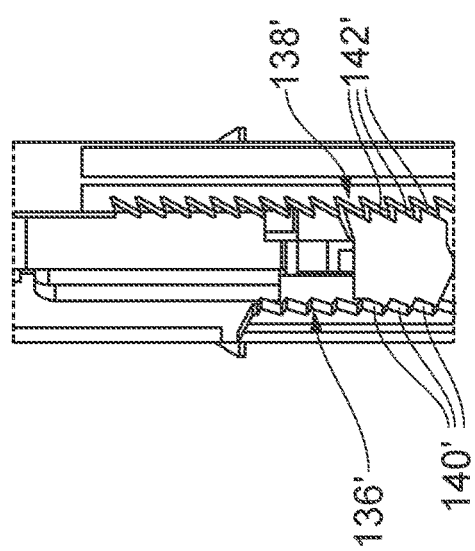

INJECTION APPARATUS

CROSS-REFERENCE TO RELATED APPLICATIONS

The present application is a divisional application of U.S. Ser. No. 16/494,074 filed Sep. 13, 2019, which is the United States National Stage of International Application No. PCT/GB2018/050673, filed on Mar. 15, 2018, which claims priority to British Patent Application Serial Nos. GB 1704141.9, GB 1704142.7, GB 1704136.9, GB 1704137.7, GB 1704143.5, and GB 1704140.1, each of which were filed on Mar. 15, 2017, the contents of which are incorporated herein by reference in their entirety.

TECHNICAL FIELD

This invention relates to an auto-injection syringe which facilitates powered or power assisted needle insertion and drug delivery.

BACKGROUND

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament such as Insulin. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an "injection apparatus" device, in which, in addition to automating the delivery of the medicament, the device may also be arranged to automate the insertion of a needle into the skin prior to the delivery of the medicament.

Injection devices generally comprise a delivery arrangement which is arranged to automatically deliver a dose from the syringe, and optionally (in the case of an injection apparatus) to first displace the syringe within the housing to cause needle penetration. The delivery arrangement generally acts via a plunger which includes or engages a piston (also referred to as a bung) which is slidably and sealably provided within the barrel of the syringe. In the case of an injection apparatus the initial static friction or "stiction" between the bung and syringe resists forward movement of the piston relative to the syringe such that initially the delivery arrangement moves the syringe and piston forward into the needle insertion position. Here, further movement of the syringe is blocked and the delivery arrangement will continue to move forward, overcoming the stiction, and moving the piston and the bung through the syringe.

A common form of delivery arrangement includes an actuation mechanism which biases the plunger forwardly and a trigger mechanism which holds the plunger (directly or indirectly) against the force of the actuation mechanism until the trigger is released. For example the actuation mechanism may comprise a delivery actuator (for example a compression spring) which is held in an energised (or primed position) prior to release by the trigger. The trigger may be activated by a user's digit. Alternatively, the device may be pressure activated in which the trigger mechanism is provided by pressured contact with the injection site, typically via a needle shield.

An injection device of the injection apparatus type is described in WO2016/189286. The actuation mechanism of this device comprises two springs, a first, relatively weak, insertion spring for moving the syringe through the device housing to insert the needle 14 into the skin and a second, relatively strong, delivery spring for driving the plunger 30 and piston through the syringe body.

WO2016/189286 addresses a known problem with injection apparatus, namely that the force exerted by the insertion spring during the needle insertion phase may be great enough to damage the syringe when it bottoms out against the housing at the end of its travel. The problem is mitigated by incorporating a velocity regulator which limits the velocity of the syringe until it has bottomed out.

A further issue with known auto-injectors, particularly pressure activated devices, is that invariably some part of the actuating mechanism is required to extend rearwards from the syringe carrier to the delivery driving assembly which is located to the rear of the syringe. This requires various components to pass the barrel which inevitably results in an increase in the width of the device.

The present disclosure seeks to provide solutions to some of the issues identified in state of the art syringes.

SUMMARY

The present invention provides an auto-injection apparatus for receiving a syringe as defined by the appended claims.

Disclosed herein is a first example of an auto-injection apparatus for receiving a syringe. The apparatus may comprise: an outer casing which encloses a drive assembly and a syringe carrier configured to hold a barrel of the syringe, the syringe carrier being forward of the drive assembly and having a stowed position and a delivery position.

An interlock may extend between the syringe carrier and a syringe carrier housing which at least partially surrounds the syringe carrier. The interlock may prevent the forward motion of the syringe carrier under the influence of an insertion actuator whilst in the stowed position.

The drive assembly may comprise the insertion actuator for inserting a needle of the syringe into an injection site and a delivery actuator for driving a plunger into a barrel of the syringe which contains a substance for injection.

The syringe carrier comprises an interlock release mechanism which is configured to release the interlock such that the insertion actuator drives the syringe carrier forward.

Providing an interlock which extends between the syringe carrier and housing, and a syringe carrier comprising an interlock release mechanism allows the actuation for activating the auto-injection to be located forward of the distal end of the syringe carrier and/or the syringe barrel. In doing so, it removes the need to have anything extending rearwards past the barrel and the diameter of the syringe can be reduced.

The interlock may have a first part on the syringe carrier and a second part on the housing. The interlock may be forward of the driving assembly. The interlock may be forward of the distal end of the syringe carrier. The interlock may comprise axially opposing surfaces which abut one another to restrict forward axial movement of the syringe carrier. The syringe carrier can include a barrel housing and a trigger. The trigger may be a shield which shrouds the needle before, during or after an injection.

The syringe carrier may comprise a barrel housing and the interlock may be provided between the barrel housing and the syringe carrier housing.

The interlock includes a syringe carrier housing stop and a syringe carrier stop which axially abut one another to prevent forward motion of the syringe carrier.

The outer casing may be or comprise the syringe carrier housing. Either or both of the housing stop and syringe carrier stop may comprise a projection which extends from a surface of the respective component. The syringe carrier housing stop and syringe carrier stop may include axially opposing surfaces which abut one another. The abutment may prevent forward axial movement of the syringe carrier when the interlock is engaged.

Either or both of the syringe carrier housing stop and the syringe carrier stop includes an elongate circumferentially extending axially facing abutment surface for engaging the other of the syringe carrier housing stop or syringe carrier stop.

The circumferentially extending axially facing abutment surface may allow a predetermined amount of relative rotation between the syringe carrier housing and syringe carrier prior to disengagement. The predetermined relative rotation may include one or more phases of activation. The phases of activation may include a injection site location phase in which the trigger may undergo axial displacement without triggering the insertion phases. The circumferentially extending axially facing abutment surface is part of an elongate rib. The elongate rib may extend circumferentially. The circumferentially extending elongate rib may comprise ramped portions.

The interlock release mechanism may include a trigger which activates the interlock release mechanism when actuated.

The trigger may be a push button trigger activated by a user. The push button trigger may be a pressure activated trigger. The pressure activation may be achieved by inserting the auto-injection apparatus against an injection site. The pressure activated trigger may be a needle shield used to sheath the needle before, during or after use.

The trigger may provide relative rotation between the syringe carrier stop and the syringe carrier housing stop.

The barrel housing may be located at least partially within the trigger.

The trigger may comprise a pressure activated trigger. The pressure activated trigger may comprise a shield which is arranged to shroud the needle prior to, during, or after an injection.

The interlock release mechanism may include a track and protrusion arrangement in which the protrusion is arranged to slide within the track such that relative movement of either of the protrusion or track causes the other of the protrusion and track to move axially and/or rotationally.

The track may be provided by a channel. The channel may form part of a wall portion of the syringe carrier or the trigger. The track may include one or more running surfaces against which the protrusion slides.

The track may include a release portion in which a rearwards axial movement of the trigger translates to a rotation of the syringe carrier stop to disengage the interlock.

The release portion may comprise a ramped portion of track which is inclined axially and circumferentially. Thus, axial movement of the track or protrusion causes a corresponding circumferential movement. The rearwards axial movement of the trigger may be provided by depressing the trigger against an injection site.

The track may further include a priming portion in which a forwards axial movement of the trigger translates to a rotation of the syringe carrier.

The forwards axial movement of the trigger may be induced by removing a cap attached to the proximal end of the auto-injection apparatus prior to use.

The track may include an axial stop to prevent the protrusion travelling axially rearwards beyond a predetermined position once the interlock has been disengaged and the trigger released.

The track includes a rotational stop arranged to allow relative axial movement between the track and protrusion but no relative rotation. The rotational stop may allow the trigger to be depressed and released multiple times without disengaging the interlock so that a suitable injection site may be located. The rotational stop may be located upstream of the release portion.

The trigger may be configured to depress by a first portion using a first force and a second portion by a second force, wherein the second force is greater than the first force.

The second portion may correspond to the release portion in which the interlock is disengaged. The first portion may correspond to the site location phase.

The drive assembly may abut the syringe carrier. The abutment may be via the barrel. The barrel may include a rearward facing surface. The rearward facing surface may define the opening of the barrel which receives the plunger during an injection. The rearward facing surface may be provided by a flange.

Prior to the interlock being released, the drive assembly may be urged forwards relative to the outer casing by a biasing member. The biasing member may comprise the insertion actuator. The insertion actuator may comprise a spring. The spring may be a compression spring. The biasing member may drive the syringe carrier forward once the interlock has been released.

The outer casing may comprise a first portion and a second portion which are attached together, and, the drive assembly may be retained by a latch in the first portion prior to the first portion being attached to the second portion and the biasing member is between the first portion and the drive assembly such that the biasing member urges the drive assembly out of the first portion of the outer casing and against the latch.

The second portion of the outer casing may be arranged to activate a latch release mechanism for disengaging the latch upon the attachment of the first portion and second portion during assembly of the outer casing such that the biasing member urges the drive assembly forwards beyond the latch once disengaged.

The latch release mechanism may be provided by an axially translatable portion of the drive assembly. The axially translatable portion may be engaged with the outer casing during the assembly of the outer casing.

The second portion of the outer casing may house the syringe carrier. The syringe carrier may include the barrel. Either or both of the syringe carrier and barrel may abut the drive assembly during the assembly of the outer casing. The abutment may drive the axially translatable portion rearwards to activate the latch release mechanism.

Where the insertion actuator provides an insertion force for inserting the needle and the delivery actuator provides a driving force for driving the plunger, the driving force may be greater than the insertion force.

There may be a plurality of channels. There may be two or more helical channels may be equidistantly distributed around the circumference of the sleeve. The firing cartridge may be nested within the sleeve.

The corresponding forward facing surface and rearward facing surface may be obliquely angled with respect to the normal of the longitudinal axis, such that the engagement surface rotate and bind together when the firing cartridge undergoes a rearward bias.

The firing pin may be activated by contacting the bung. The firing cartridge may include a back portion. The back portion may be located at a distal end of the firing cartridge. The back portion and plunger may form a housing for the delivery actuator. The back portion and plunger may be axially engaged. The axial engagement may be interlocked via the firing pin. The plunger and back portion may be engaged via a bayonet fitting. The bayonet fitting may include an axial part and a circumferential part. The circumferential part may include an axially inclined circumferential seat. The axial part may provide a gateway to the circumferential part. The firing pin may be located within the axial part so as to at least partially block the circumferential path. The firing pin may pass through the plunger. The firing pin may pass along the centre of the plunger. The firing pin may slide longitudinally within the firing pin.

The activation of the delivery actuator may drive the bung along the interior of the barrel so as to carry out the injection. The bung may be driven by the delivery actuator via a plunger. The delivery actuator may be located within the plunger. The firing cartridge may comprise a plunger and a firing pin. The firing pin may pass through the firing cartridge.

Also disclosed herein is a second example of an injection apparatus which may comprise: an outer casing; a syringe carrier housed within a forward portion of the outer casing; a firing cartridge housed rearwards of the syringe carrier in the outer casing in which the firing cartridge may be configured to move between a stowed position and a delivery position and comprising a delivery actuator arranged to drive the bung within the barrel so as to carry out an injection.

The injection apparatus of the second example may further comprise: a priming arrangement configured to drive the firing cartridge forwards within the outer casing to provide contact between the firing cartridge and bung prior to the delivery actuator being activated.

There is also the broad disclosure of a third exemplary injection apparatus for receiving a syringe which comprises: an outer casing; a syringe carrier housed within a forward portion of the outer casing; a firing cartridge housed rearwards of the syringe carrier in the outer casing. The firing cartridge may be configured to move from a first position rearwards and separated from a bung of the syringe to a second position in which the firing cartridge contacts the bung. The firing cartridge may be configured to expand so as to drive the bung through a barrel of the syringe when in the second position.

The firing cartridge may comprise: a plunger arranged to drive the bung within the barrel of the syringe so as to carry out an injection; a back portion detachably attached to the plunger to provide a housing for a delivery actuator; a firing mechanism arranged to detach the back portion from the plunger when the firing mechanism contacts the bung.

The injection apparatus may further comprise: a priming arrangement configured to drive the firing cartridge forwards within the outer casing to provide contact between the firing mechanism and bung prior to the delivery actuator being activated.

The disclosure also includes a fourth example of an injection apparatus which comprises: an outer casing; a syringe carrier housed within a forward portion of the outer casing and arranged to receive a barrel of a syringe; and a drive assembly rearwards of the syringe carrier within the outer casing. The drive assembly may be arranged to drive a bung within a barrel of the syringe. The barrel and outer casing may be directly adjacent to one another around the full periphery of the distal end of the barrel in that no part of the syringe carrier passes rearwards beyond the distal end of the barrel. Additionally or alternatively, no part of the drive assembly passes forwards past the radial outside of the distal end of the barrel.

A fifth example of an auto-injection apparatus for receiving a syringe is disclosed and may comprise: an outer casing; a syringe carrier housed within the outer casing and configured to hold a barrel of the syringe; and, a drive assembly housed in the outer casing rearwards of the syringe carrier.

The drive assembly may comprise: a firing cartridge and a sleeve in which the firing cartridge is located, wherein the firing cartridge is configured to move forwards between a stowed position and a delivery position and may comprise: a drive actuator; a guide surface runner; and, a cartridge backstop.

The sleeve may comprise at least one rearward facing guide surface for engagement with the guide surface runner so as to direct the forward movement of the firing cartridge from the stowed position to the delivery position. A sleeve backstop which may engage the cartridge backstop against the plunger can react to drive forwards when the firing cartridge is in the delivery position.

The sleeve comprises a channel having opposing first and second edges. The first edge may be a guide edge comprising the at least one guide surface. The second edge may be a backstop edge comprising a plurality of the sleeve backstops distributed along a length thereof. The channel(s) may extend axially.

The auto-injection apparatus of the fifth example may comprise a plurality of channels circumferentially distributed around the sleeve.

At least one of the plurality of sleeve backstops may be axially rearwards of a portion of the at least one guide surface.

The or each sleeve backstop may include a forward facing surface which engages with a corresponding rearward facing surface of the cartridge backstop.

The firing cartridge may further comprise a plunger which engages with a bung of the syringe to drive it forwards, and a firing pin which activates the drive actuator.

The firing cartridge may include a first part and a second part which are detachably attached via a coupling and the drive actuator may be located within the firing cartridge; wherein decoupling the first part and second part of the coupling results in the drive actuator driving the plunger axially forwards. The coupling may comprise a bayonet fitting.

The guide surface runner and the cartridge backstop may be located on a guide member which is located within the channel and attached to the firing cartridge.

The auto-injection apparatus of the fifth example may comprise a plurality of guide surfaces and the guide surfaces may be descending guide surfaces provided on both of the guide edge and backstop edge. The plurality of descending guide surfaces may face rearwards into the channel. The guide member may include a first guide surface runner for engaging with the descending guide surfaces of the guide edge, and a second guide surface runner for engaging with the descending guide surfaces of the backstop edge.

The guide edge may comprise a plurality of guide edge teeth and the backstop edge comprise a plurality of backstop teeth. The guide edge teeth and backstop teeth may comprise the plurality of descending guide surfaces and are distributed along the length of the respective edge. The guide member may be arranged to laterally oscillate between the descending surfaces of the guide edge teeth and the backstop teeth as the firing cartridge moves forward from the stowed position to the delivery position.

The guide edge teeth may further comprise a lead-on guide surface which faces forwards and into the channel. The lead-on guide surface may be arranged to direct the cartridge backstop towards the sleeve backstop upon rearwards movement of the guide member within the channel.

The guide edge teeth and backstop edge teeth may have different profiles when viewed from radially inwards direction.

The guide edge teeth and backstop edge teeth may have the same profile. The teeth may be symmetrical with respect to a longitudinally extending plane. Thus, the teeth may be mirror images about the longitudinal axis of the syringe.

The backstop edge teeth may comprise the sleeve backstop and the backstop edge teeth are tapered such that the sleeve backstop and descending surface are separated by an acute internal angle.

The guide edge teeth and backstop edge teeth may be axially offset from one another. The pitch and peak to trough of the backstop edge teeth and guide edge teeth may be the same.

The lead-on surface and the backstop edge descending guide surface may be anti-parallel.

Then auto-injection apparatus of the fifth example may comprise: a priming arrangement configured to drive the firing cartridge forwards within the sleeve and along the guide surface to provide contact between the firing cartridge and bung, thereby placing the firing cartridge in the delivery position prior to the delivery actuator being activated.

The priming arrangement may comprise the insertion actuator. The channel may be helical.

The guide surface may provide axial alignment between the sleeve backstop and the cartridge backstop during movement of the firing cartridge from the stowed position to the delivery position.

A sixth example of the an auto-injection apparatus may comprise: an outer casing comprising a first portion and a second portion which are attached together for use, wherein the outer casing houses a drive assembly and a syringe carrier configured to hold a barrel of the syringe, the syringe carrier being forward of the drive assembly and having a stowed position and a delivery position.

The drive assembly may be retained by a latch in the first portion of the outer casing prior to the first portion being attached to the second portion. A biasing member may be located between the first portion and the drive assembly and arranged to urge the drive assembly out of the first portion and against the latch.

The auto-injection apparatus of the sixth example may also comprise a latch release mechanism for disengaging the latch upon the attachment of the first portion and the second portion during assembly of the outer casing such that the biasing member urges the drive assembly forwards beyond the latch once the latch has been disengaged.

The drive assembly may comprise a firing cartridge and a sleeve in which the firing cartridge is located.

The latch may be a resiliently deformable tab which extends radially inwards from the first portion. The tab may engages with the axially forward facing surface of the drive assembly. The firing cartridge may comprise the axially forward facing surface.

The firing cartridge may comprise a guide member for guiding the firing cartridge from a first position to a second position within the outer casing. The guide member may comprise the axially forward facing surface.

The latch release mechanism may comprise an axially translatable portion of the drive assembly. The axially translatable portion may be arranged to move rearward with the second portion as the first and second portions are attached during assembly.

The auto-injector may further comprise: a syringe carrier housed within the second portion and configured to hold a barrel of the syringe; and the axially translatable portion contacts syringe carrier or barrel so as to be pushed rearwards with the second portion during assembly. The axially translatable portion may comprise the sleeve.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein. For example, it will be appreciated that the syringe carrier 26 and interlock 54 arrangement may be used within a syringe which does not include one of the described a drive assemblies, or vice versa.

BRIEF DESCRIPTION OF THE DRAWINGS

Examples of injection apparatus 10es will now be described, with reference to the Figures, in which.

DETAILED DESCRIPTION

Figure 1A:
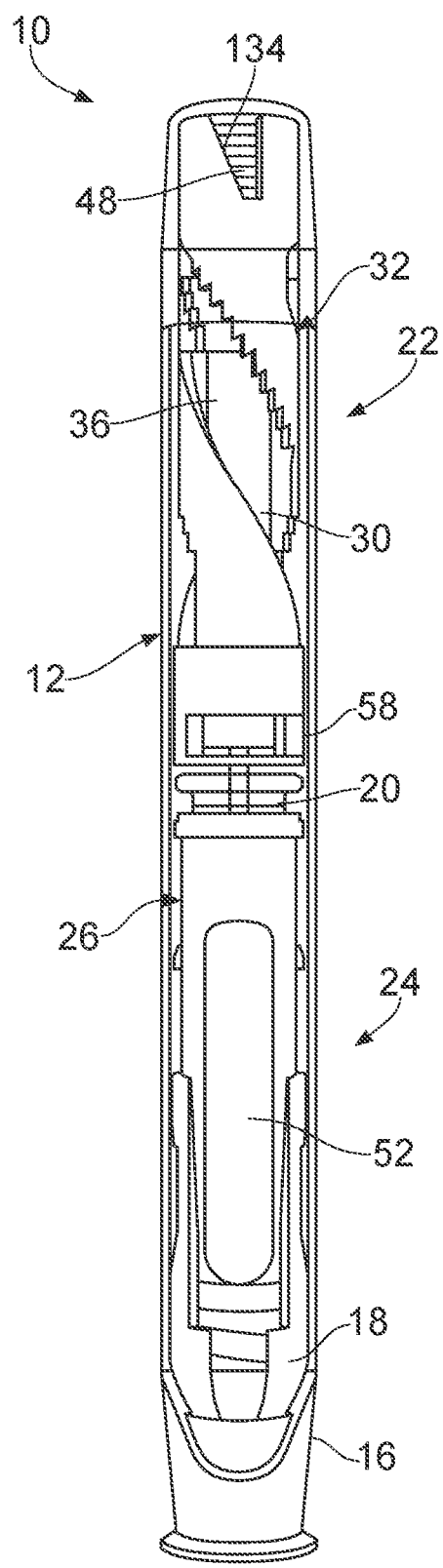
FIGS. 1a and 1b show a side view and longitudinal section of an injection apparatus 10.
Figure 1B:
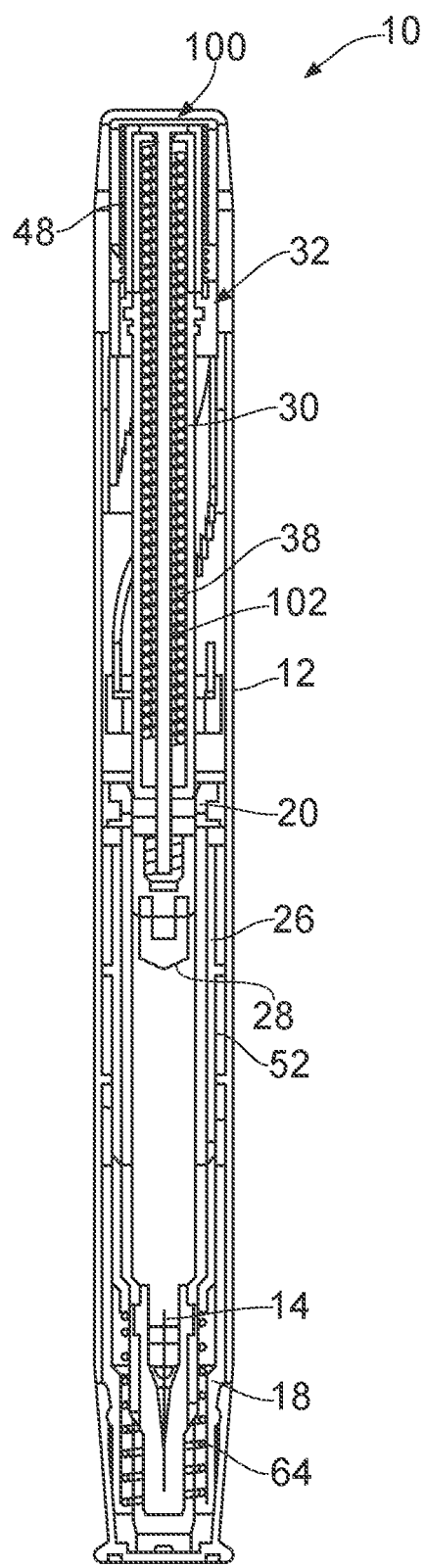

FIGS. 1a and 1b show a side view and longitudinal section of an injection apparatus 10. The side view includes an outer casing 12 which is shown partially transparent to reveal the inner workings of the injection apparatus 10.

The injection apparatus 10 includes a syringe which comprises a needle 14 for insertion into an injection site for injection of a substance, typically a medicament, into an injection site. The injection apparatus 10 may be considered automatic in that some of the injection operations require a single user operation and may be referred to as an auto-injector apparatus, an auto-injector or an auto-injection syringe. For example, the user may be required to remove a cap 16 which covers the needle 14, locate a suitable injection site before applying suitable inwards pressure to the housing or depressing a trigger to activate the syringe. Activation may result in an automated, typically mechanised, sequence including needle insertion and injection of a solution from the syringe into the injection site without further action from the user. Subsequent withdrawal of the needle 14 may result in a shield 18 being deployed to cover the needle 14 to allow for safe handling after use. The shield 18 may be locked out to prevent accidental or purposeful retraction of the shield after being deployed. In some syringe apparatuses, the insertion may be carried out manually, with only the injection phase being automated.

It will be appreciated that although the injection apparatus 10 described below includes the description of the syringe with the barrel 20 and solution/medicament, the injection apparatus 10 may be supplied without the syringe. Similarly, the syringe may be provided with or without a needle 14 attached. Further, the injection apparatus 10 may be provided as a modular system such as a kit of parts which can be assembled by an end user or an intermediary. The kit of parts may include any or all of the separate parts of the outer casing, the syringe carrier, the syringe, the drive assembly and the insertion spring (which also provides a priming actuator in some examples).

The injection apparatus 10 is generally an elongate cylindrical structure having a longitudinal axis with a proximal or front end denoted by the needle 14, and an opposing distal or rear end. The outer casing of the cylindrical structure is generally held by the user during use. References to radial and axial in this specification should be taken in relation to the longitudinal axis unless otherwise stated. The term axis can be taken to be the longitudinal axis of the device unless otherwise stated or obvious from the context. The normal of the longitudinal axis is taken to be perpendicular to the longitudinal axis.

The principal components of the injection apparatus 10 may include an outer casing 12, a rear sub-assembly 22 and a front sub-assembly 24. The two sub-assemblies may be considered to be separate in as much as they are functionally separate and/or are physically separate outside being abutted within the casing. The two sub-assemblies may be individually assembled and loaded into the outer casing 12, prior to the outer casing 12 being assembled. The front 24 and rear 22 sub-assemblies may abut one another via the barrel 20.

The outer casing 12 generally defines the exterior of the injection apparatus 10 and provides an internal cavity in which the constituent parts, such as the rear sub-assembly 22 and front sub-assembly, can be enclosed. Thus, the outer casing 12 provides a housing and may be referred to as such. The housing may be provided by a unitary body which forms the outer casing 12, or may comprise distinct parts or sections which are axially engaged and/or co-axially nested.

The front sub-assembly 24 includes a syringe carrier 26 in which the syringe is carried. The syringe may be conventional in that it includes a barrel 20 with a piston which is slidably and sealably received from an open distal end. The piston may include a bung 28 which engages with the barrel 20, and a plunger 30 which drives the bung 28.

A needle 14 for injection into an injection site is attached to the proximal end of the syringe barrel 20 by a suitable attachment as well known in the art. The attachment may be fixed or detachable. The plunger 30 is located at a distal first position prior to injection and is driven forwards during use to a proximal second position. The travel of the plunger 30 is determined by the travel of the bung 28 required to eject the solution and may be coterminous with the closed end of the barrel 20 to which the needle 14 is attached. FIG. 1b shows the position of the bung 28 at the first position, prior to the injection.

The proximal end of the injection apparatus 10 may terminate in a removable cap 16 which covers and protects the needle 14 in transit and prior to use.

The rear sub-assembly 22 may include a drive assembly 32 arranged to drive the plunger 30 into the barrel 20 to carry out the injection. The rear sub-assembly 22 may additionally provide an insertion actuator 48 for inserting the needle 14 into an injection site, where auto-insertion is required. Additionally, the rear sub-assembly 22 may include a priming arrangement for moving the plunger 30 into a delivery position from a stowed position.

In the example shown in FIGS. 1a and 1b, the rear sub-assembly 22 comprises a multi-functional drive assembly 32. The drive assembly 32 is primarily used to carry out the injection once the needle 14 has been inserted by driving the bung 28 forwards within the barrel 20 from a distal first position to a proximal second position. In this example, the drive assembly 32 is also used to drive the syringe forward to provide insertion of the needle 14 into the injection site. the drive assembly 32 may also include a priming arrangement for moving the plunger 30 from a stowed position to a delivery position.

The insertion and delivery may be carried out by the same or different actuation mechanisms. In the example shown in FIGS. 1a and 1b, the insertion is carried out by an insertion actuator 48 in the form of an insertion spring. The delivery is carried out by a delivery actuator 38 in the form of a delivery spring. The insertion and delivery springs will typically be compression springs but other suitable springs and actuators may be used where applicable.

The drive assembly 32 may include a firing cartridge 36. The firing cartridge 36 is movable from a stowed position, in which it resides until activated, to a pre-delivery position from where the plunger 30 is driven into the barrel 20 of the syringe to push the bung 28 forwards and carry out the injection. The movement of the firing cartridge 36 from the stowed position to the pre-delivery position may be carried out by the priming arrangement. The priming arrangement may include a priming actuator which provides a driving force between the housing, e.g. the outer casing 12, in which the driving arrangement is located, and the firing cartridge 36.

In particular, the movement from the stowed position may be carried out by the insertion actuator 48. Thus, the insertion actuator 48 may be used to provide insertion of the needle 14 by moving the syringe carrier 26 forwards within the outer casing 12, and also move the firing cartridge 36 forward independently of the syringe carrier 26, thereby acting as a priming actuator.

The movement of the firing cartridge 36 from the stowed position to the pre-delivery position may be relative to the outer casing 12 and/or other elements of the drive assembly 32. Hence, the outer casing 12 and/or drive assembly 32 may be considered to be stationary whilst the firing cartridge 36 is driven forwards from the stowed position to the pre-delivery position.

Moving the firing cartridge between the positions may requiring moving the firing cartridge 36 axially forwards within the outer casing 12 to reduce the distance between the syringe and the delivery actuator 38 which is used to drive the bung 28 within the barrel 20 once activated. Reducing the axial separation between the syringe and the plunger 30 may be beneficial. It may reduce the amount of impacting force between the syringe and the plunger 30 which can reduce the instances of either the syringe or plunger 30 suffering damage during activation. Further, it can also allow for syringes having different fill levels to be used in a common device. Thus, the injection apparatus may be configured to accept one or more conventionally dimensioned syringes, whilst being able to adjust the amount of medicament which is required for delivered. For example, a syringe of a given sized barrel 20 may be used to deliver a 0.5 ml dose in which the bung 28 is located half-way up the barrel 20, and a 1 ml dose in which the bung 28 is located towards the distal end of the barrel 20. A yet further advantage is that the delivery actuator 38 can be provided with a higher driving force such that solutions having different viscosities can be delivered by the common syringe.

The firing cartridge 36 may include: a delivery actuator 38 and a plunger 30. The delivery actuator 38 may be arranged to drive the plunger 30 forwards when in engagement with the bung 28.

It will be appreciated that the priming arrangement which moves the firing cartridge 36 forwards within the outer casing 12 may exert a smaller force than the delivery actuation. Thus, the force at which the priming arrangement allows a lower contacting force between the bung 28 and plunger 30 reducing the likelihood of damage, whilst a strong driving force can be provided.

The front sub-assembly 24 may comprise a syringe carrier 26. The syringe carrier 26 is arranged to carry the syringe, which includes a barrel 20 and a bung 28, within a barrel housing 52. In order to provide insertion of the needle 14 into the injection site, the syringe carrier 26 may be moved from a stowed position to an injection/delivery position in which the needle 14 projects from the distal end of the outer casing 12.

The forward movement of the syringe carrier 26 into the delivery position may be prevented by an interlock 54. The interlock 54 may comprise one or more elements of the syringe carrier 26. The syringe carrier 26 may additionally or alternatively include an interlock release mechanism 56.

The interlock 54 may be provided between the syringe carrier 26 and a syringe carrier housing 58. The syringe carrier housing 58 may be, or be part of, the outer casing 12 and will at least partially surround the syringe carrier 26.

The interlock 54 may have a first part on the syringe carrier 26 and a second part on the housing. The interlock 54 may be forward of the driving assembly. Hence, the interlock 54 may be forward of the distal end of the syringe carrier 26 such that no part of the interlock 54 is located aft of the barrel 20. The interlock 54 may comprise axially opposing surfaces which abut one another to restrict forward axial movement of the syringe carrier 26.

The interlock 54 may include a first stop 60 and a second stop 62 which axially abut one another to prevent forward motion of the syringe carrier 26 within the outer casing 12. The first 60 and second 62 stops may be respectively located on the syringe carrier housing 58 and syringe carrier 26. Either or both of the first 60 and second 62 stops may comprise a projection which extends from a surface of the respective component. Either or both of the syringe carrier housing stop 60 and the syringe carrier stop 62 may include an elongate circumferentially extending axially facing abutment surface 68.

The example shown in FIGS. 1*a* and 1*b* includes a shield 18 arrangement which is used to shroud the needle 14 prior to, during or after an injection has taken place. The shield 18 may be a lock out shield in which a shield/sheath is locked in an extended position after use. The shield 18 may be used as a trigger in a pressure activated device as is the case for the example shown in FIGS. 1*a* and 1*b*. The shield 18 may be connected to and move with the syringe carrier 26 and form part of the syringe carrier 26. The movement of the shield 18 and/or syringe carrier 26 may be relative movement such that the syringe carrier 26 and shield 18 are both moveable relative to the outer casing 12 and to each other.

The shield 18 may be deployed with the assistance of a shield actuator which may take the form of a compression spring, as shown. The shield actuator may be referred to as the lock-out spring 64.

The cap 16 which shrouds the proximal end of the injection device prior to use may form part of the interlock release mechanism 56.

Figure 2:
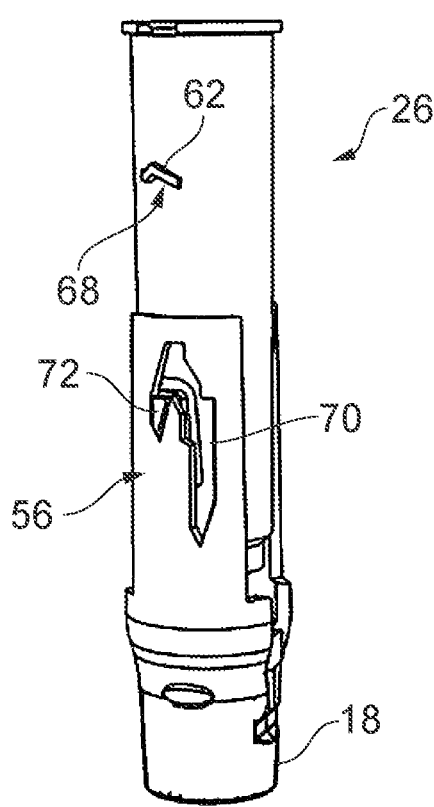
FIG. 2 shows a perspective view of a syringe carrier.
Figure 3:
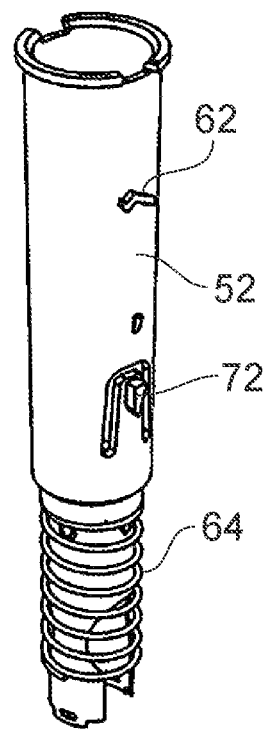
FIG. 3 shows a perspective view of a barrel housing.

FIGS. 2 and 3 shows an example of a syringe carrier 26 and some of its constituent parts. The syringe carrier 26 includes a barrel housing 52 which provides a receptacle for the syringe barrel 20. The main body of the barrel housing 52 is generally cylindrical having an internal surface which corresponds to the outer surface of a barrel against which it mates. The outer surface of the barrel housing 52 incorporates various features relating to the interlock 54 and interlock release mechanism 56. The distal end of the syringe carrier 26 is open-ended to receive the barrel 20 of the syringe. There may be examples where the syringe carrier 26 and syringe are a single part in that the outer surface of the syringe and/or syringe barrel may include the interlock 54 and interlock release mechanism 56 features.

The syringe carrier 26 forms part of an interlock 54 which prevents forward axial movement of the syringe carrier 26 under the influence of the driving assembly or otherwise. The interlock 54 is provided by axially engaging features on corresponding parts of the syringe carrier 26 and a housing which is located radially outside of the syringe carrier 26.

The axially engaging feature is provided in the form of a pair of stops which abut one another. There may be a syringe carrier housing stop 60 and a syringe carrier stop 62.

Figures 6A, 6B:
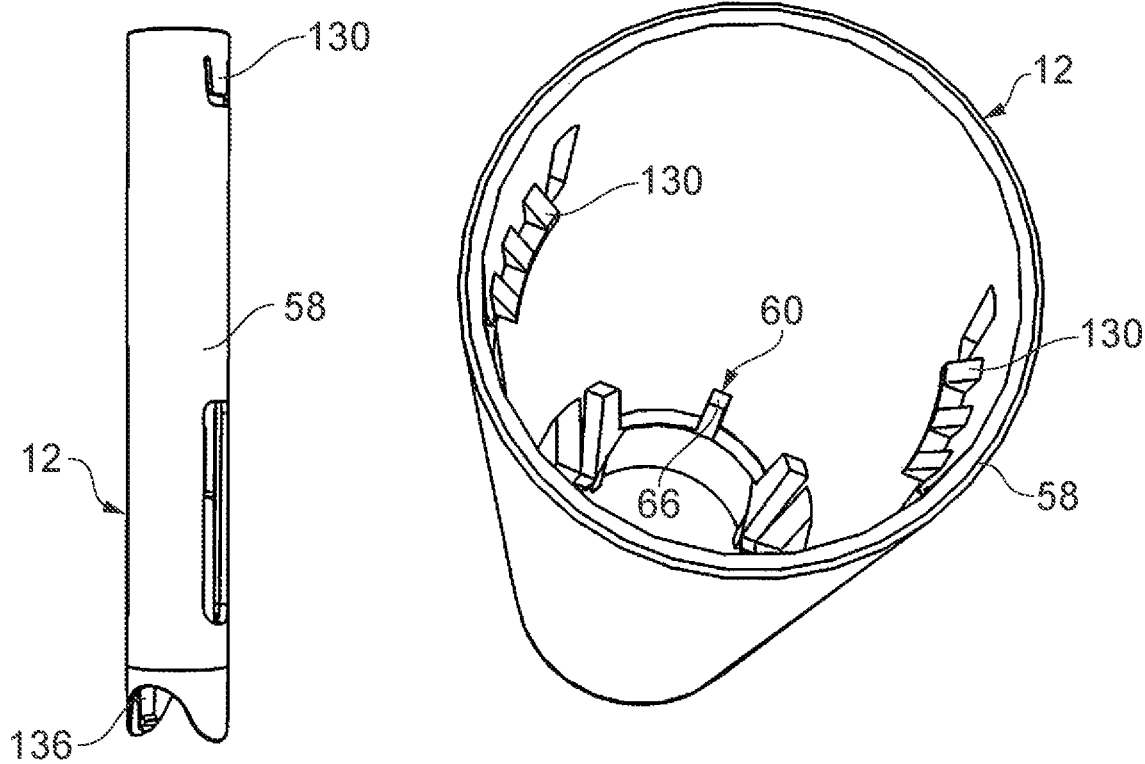
FIGS. 6a and 6b show a side view and perspective internal view of a portion of the outer casing.

The syringe carrier housing stop 60 may be formed on an inner wall of the outer casing 12 and may be provided by a projection which extends from the internal surface of the inner wall of the outer casing 12 as shown in FIG. 6*b*, which shows the interior of the outer casing 12. The syringe carrier housing stop 60 may include a first stop surface which faces the distal end of the injection apparatus 10 to provide an abutment surface for preventing axially forwards movement of the syringe carrier 26. In FIG. 6*b*, the syringe carrier housing stop 60 is provided by an elongate structure in the form of a rib with a housing abutment surface 66 provided by distal end face of the rib. As shown, the rib may extend axially along the wall of the housing.

The syringe carrier stop 62 may also be a projection which extends from a surface of the syringe carrier 26. The syringe carrier stop 62 may be an elongate structure in the form of a rib. As shown, the rib may extend circumferentially around a radially outer wall of the syringe carrier 26. The wall may be that of the barrel housing 52. The syringe carrier stop 62 includes a second stop surface which faces the proximal end of the injection apparatus 10 to provide a carrier abutment surface 68 for engagement with the housing abutment surface 66 of the syringe carrier housing stop 60, thereby preventing axially forwards movement of the syringe carrier 26 whilst the two stops are circumferentially aligned.

Rotating the syringe carrier 26 about the longitudinal axis of the injection device relative to the housing separates the two stops 60, 62 such that they no longer axially overlap. At this point, the syringe carrier 26 may move forwards within the outer casing 12. In some examples, this results in the insertion phase of the injection apparatus 10 where the needle 14 is driven axially forwards and outside of the outer casing 12. It will be appreciated that in some examples, there may be additional steps within the activation of the injection apparatus 10 which may occur prior to or after the disengagement of the interlock 54.

Either or both of the syringe carrier housing stop 60 and the syringe carrier stop 62 may include an elongate circumferentially extending axially facing abutment surface which engage with the other stop to permit a predetermined amount of relative rotation prior to disengagement. The surface(s) 66, 68 may be provided by any suitable surface such as a wall, rib, ridge, lip, shoulder or channel, for example.

As shown in FIGS. 9a-9e in more detail, the syringe carrier stop 62 may usefully be divided into sections which correspond to the activation steps of the injection apparatus 10. The individual sections may be denoted by ramped portions in which the angle at which the surface is inclined with respect to the normal of the longitudinal axis is different. Adjacent sections of the surface may have different angles to provide discontinuities or sections to the rotation of the syringe carrier. The function of each of the sections is described below in connection with FIGS. 9a to 9e. It will be appreciated that a surface may have multiple ramped portions and that the ramped portions may be forwards or rearwards with respect to the relative movement of the syringe carrier housing stop. The angles may be negative, positive or zero in relation to the normal of the longitudinal axis. There may be a first ramp rearwards ramp, a second forwards ramp and a third rearwards ramp. The ramps may aid or cause rotation of the syringe carrier relative to the outer casing.

The syringe carrier 26 may also include all or part of an interlock release mechanism 56. The interlock release mechanism 56 may be arranged to rotate a portion of the syringe carrier 26 such that the interlock 54 is disengaged to allow forward movement of the syringe carrier 26, or a part thereof. The arrangement of the interlock mechanism will vary as to the trigger which is required to activate the interlock release mechanism 56. Different triggers may include a push-button type actuator in which a user is required to depress a button, or a so-called 'pressure activated' actuator in which the trigger is located towards a proximal end of the syringe and is moved rearwards by the user pushing the syringe into an injection site. The pressure activated actuator is typically provided by a shield 18 which surrounds the needle 14. The shield 18 may project from the proximal end so as to provide a terminal end and first contact point for engagement with an injection site.

In the example of FIGS. 2 to 5, the interlock release mechanism 56 includes the barrel housing 52 and a lock-out shield 18. The barrel housing 52 is located at least partially within the lock-out shield 18 such that the two components axially overlap. The axial overlap between the barrel housing 52 and lock-out shield 18 provide an interface which may incorporate the interlock release mechanism 56 features, as shown. It will be appreciated that in some examples, the shield 18 may not be a lock-out shield 18 and, further, the trigger may be provided by some other component which extends proximally to contact the injection site in an appropriate manner.

In the example shown, the interlock release mechanism 56 includes a track 70 into which a protrusion 72, is received. The track 70 and protrusion 72 engage with one another such that the protrusion 72 can travel along the track 70 as the barrel housing 52 and lock-out shield 18 are moved relative to each other. The relative movement may be rotational or axial with respect to the longitudinal axis.

Either of the track 70 and protrusion 72 may be positioned on either of the lock-out shield 18 or barrel housing 52, and it will be appreciated that it is the relative arrangement which is of principal importance. However, having the protrusion 72 on the exterior of the barrel housing 52 may be preferable for assembly and operation of the interlock release mechanism 58.

The track 70 and protrusion 72 are arranged such that the portion of the syringe carrier 26 which includes the interlock 54 is rotated relative to the syringe carrier housing 58 to disengage the interlock 54. In the example shown, the track 70 is provided by an elongate channel in or on the wall of the lock out shield 18. The track 70 comprises of at least one release portion 74 which causes the syringe carrier 26 to rotate and disengage the interlock 54 when the track is axially displaced by a predetermined amount.

The release portion 74 may include a running surface 76 (or release surface) which is obliquely angled with respect to the axial direction. It will be appreciated that the specific angle of the release portion 74 relative to the axial direction will determine the ratio of the axial displacement of the lock-out shroud to the rotational displacement of the syringe carrier 26 and the force required to actuate the rotation. The running surface 76 may be any surface against which the protrusion 72 actuably slides.

The track 70 may comprise additional portions to carry out different functions within the activation process. One portion of the track 70 may provide a park position 78 in which the shield 18 may be locked out.

Figure 4:
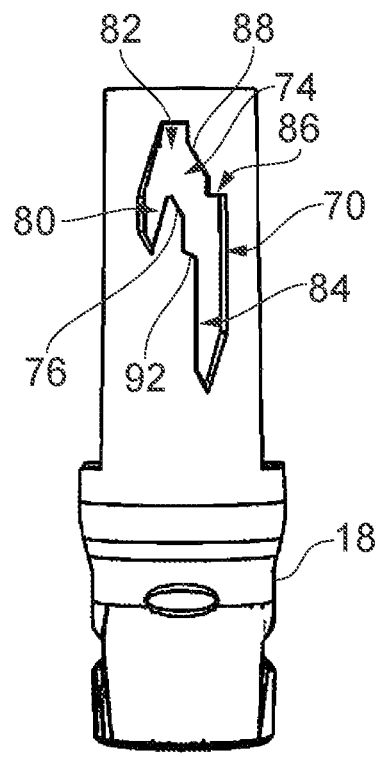
FIG. 4 shows a side view of an interlock release mechanism track.
Figure 5:
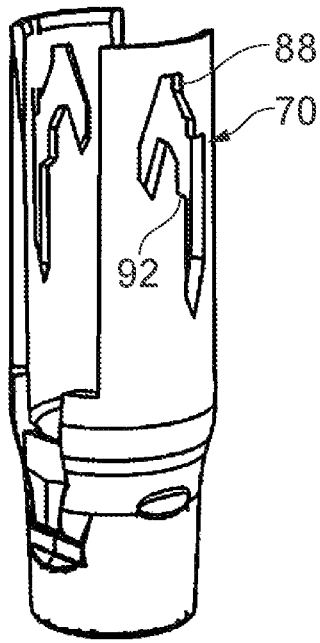
FIG. 5 shows a perspective view of a shield which includes the interlock release mechanism track of FIG. 4.

The track 70 shown in FIG. 4 principally comprises two legs which are joined together at corresponding ends thereof to provide an apex. One of the legs may be longer than the other giving the track 70 a J or hook shaped appearance when viewed radially inwards from the exterior. The protrusion 72 travels from a first end of the track 70 to a second end during the activation of the injection process.

The first portion 80 of the track 70 may provide a priming section in which the lock out shield 18 is moved forwards to be placed in a primed position ready for locating an injection site and activation. A second portion 82 of the track 70 may be arranged to provide a site location portion in which the lock-out shield 18 can be moved in and out of the device with a relatively small displacement such that suitable injection site can be found without triggering the device. A third portion 84 of the track 70 may correspond to the release and delivery portion. A fourth portion 86 of the track 70 may correspond to the parked portion to allow the lock out shield 18 to be stored.

Thus, the track 70 may have a series arrangement of portions which provide different functions in relation to the priming and activation of the injection apparatus 10. Where any of the first, second and fourth portions of the track 70 are omitted, the other portions may of course be renumbered accordingly.

The protrusion 72 is provided by an elevated portion of the barrel housing 52 wall. From a plan view (radially inwards from the exterior of the barrel housing 52), the protrusion 72 is polygonal in shape with different sides providing running surfaces for actuably engaging with the corresponding track surface as the protrusion 72 passes around the track 70. A forward portion of the protrusion 72 includes a taper which positively locates the protrusion 72 at the either extreme end of the track 70 so as to provide accurate angular and axial location of the barrel housing 52 in relation to the lock-out shield 18.

The interlock release mechanism 56 will now be described in relation to FIGS. 9a to 9e, which show the various stages of operation in conjunction with the interlock 54.

The interlock 54 includes the syringe carrier stop 62 in the form of the circumferentially extending rib on the surface of the barrel housing 52 which provides the abutment surface 68 for engagement with the syringe carrier housing stop 60. The syringe carrier stop 62 includes a plurality of ramped sections which are provided by portions of abutment surface 68 which are obliquely angled with respect to the normal of the longitudinal axis. There are three sections to the syringe carrier stop 62 shown in FIGS. 4 and 9a to 9e.

The interlock 54 may be comprised of one or more pairs of stops distributed around the syringe carrier housing. The example provides a pair of diametrically opposed stop pairs but this need not be limiting and different numbers of stops may be used.

Figure 9A:
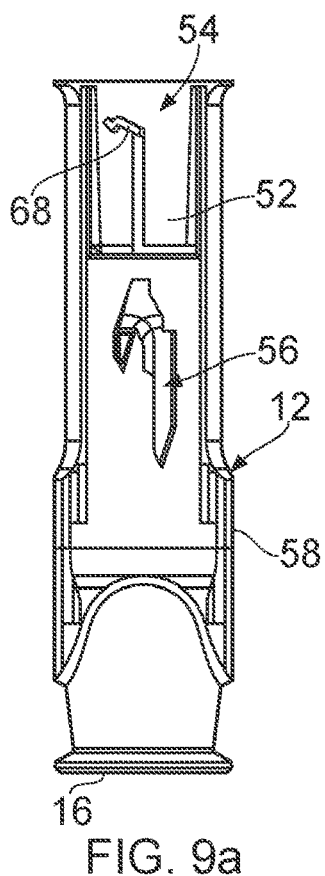
FIGS. 9a to 9e show the operational stages of a syringe carrier interlock and interlock release mechanism.
Figure 9B:
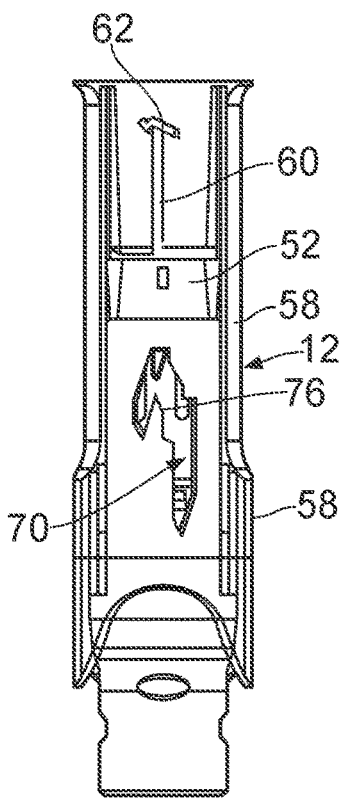
Figure 9C:
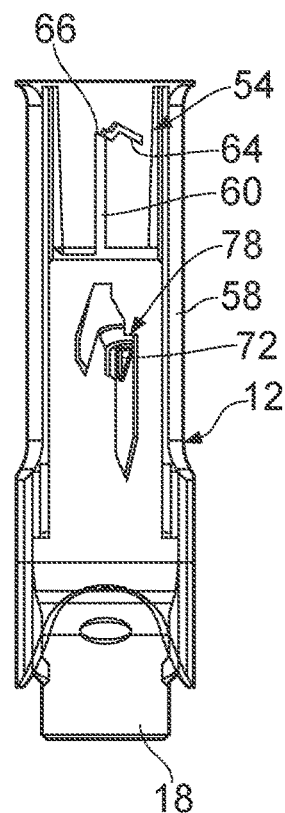
Figure 9D:
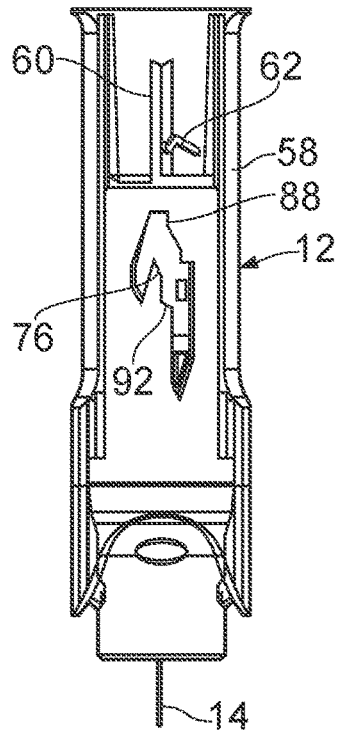
Figure 9E:
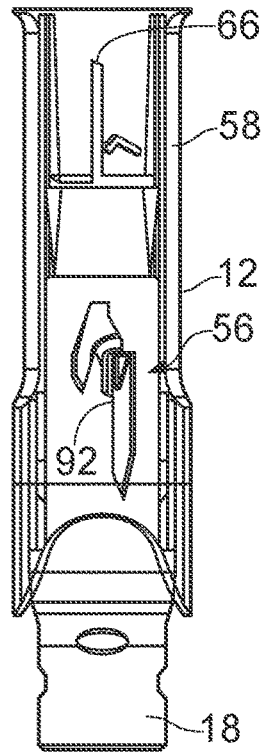

FIG. 9a shows the device prior to use, FIG. 9b shows the cap 16 removal, FIG. 9c shows the activation phase, FIG. 9d shows the delivery phase and FIG. 9e shows lock-out.

In FIG. 9a there is shown the assembled device prior to being activated. Thus, the cap 16 is still attached to the outer casing 12. Here, the protrusion 72 is placed at the first end of the track 70 with the taper of the protrusion 72 firmly received within the corresponding shape of the track 70.

FIG. 9b shows the cap 16 removed. The cap 16 is coupled to the lock out shield 18 with a gripping latch arrangement. The retaining force of the gripping latch attachment is sufficient to retain the cap on the lock-out shield 18 and or outer casing 12. The lock-out shield 18 is continuously biased against a pair of lock-out arms 136 located against a proximal surface of the shield 18. The lock-out arms 136 are held against the side of the shield 18 and prevent forward motion thereof whilst the cap 16 is in place. Once the cap 16 is removed, the shield is urged forward under the influence of the lock-out spring 64 which results in the arms 136 being pushed outwards to release the shield 18. The lock-out arms 136 are also used to lock the shield 18 in an extended position after use to protect against stick injuries. The travel of the lock-out shield 18 is limited by the end of the travel permitted by the interlock release mechanism 56.

Figure 7:
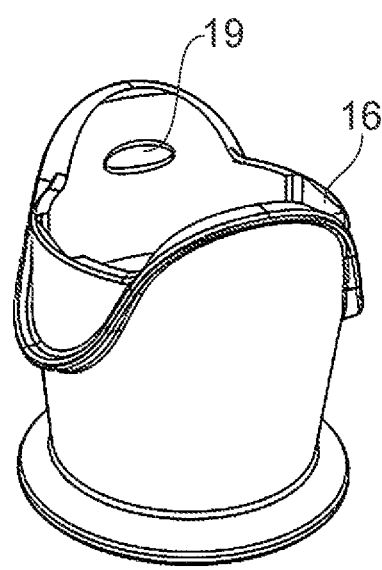
FIG. 7 shows a cap which encloses the proximal end of the injection apparatus.
Figure 8:
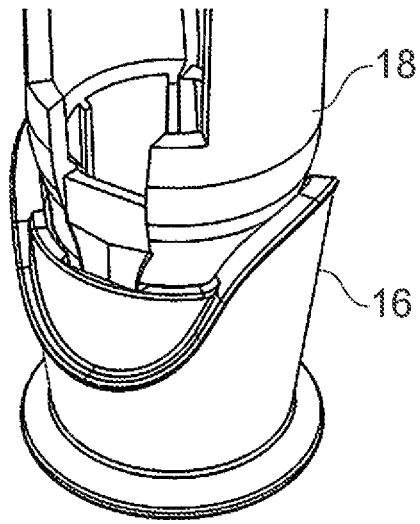
FIG. 8 shows the cap engaged with a needle shield prior to use.

The gripping latch arrangement is provided by smooth mounds on one or other of the cap 16 and shield 18 which correspond to and are mateably received within corresponding dished depressions 19 in the other of the cap 16 or shield 18, as seen in FIGS. 7 and 8. In order to facilitate the decoupling of the gripping latch arrangement, either or both of the cap 16 and shield 18 may be configured to flex when the two components are being axially displaced.

Removing the cap 16 draws the shield 18 from the outer casing 12 into a deployed position before the cap 16 disconnects for setting aside, leaving the exposed end of the device with the needle sheathed by the shield 18. The withdrawal may be assisted by a lock-out shield spring which surrounds a distal portion of the lock-out shield 18 and reacts against the outer casing 12.

The withdrawal of the shield 18 causes the track 70 to axially translate relative to the syringe carrier 26 and outer casing 12. The axial translation causes the protrusion 72 to contact with an inclined surface of the first track portion which imparts a rotation force on the syringe carrier 26. The axial displacement continues until the protrusion 72 abuts the terminal end of the first portion of the track 70. The terminal end of the first portion may be provided by a socket which snugly receives the protrusion 72 to prevent further rotation of the syringe carrier 26. The abutting surfaces between the protrusion and terminal end may be normal to the axial direction.

The rotation of the syringe carrier 26 induced by the movement of the shield 18 is relative to the syringe carrier housing 58 which causes the interlock stops to slide relative to each other. The travel is from a first point at the beginning of the first section of the ramped abutment surface 68, to an apex provided between the ramps of the first section and a second section. The incline of the first portion of the barrel housing stop allows the syringe carrier 26 to move forwards slightly within the outer casing 12 under the force of the insertion spring located in the rear of the device, which is described in detail below.

The terminal end of the second portion of the track includes an anti-rotation feature 88 which allows a predetermined amount of axial movement of the lock-out shield 18 without rotation of the syringe carrier 26. The anti-rotation feature 88 may be an axial surface of the track 70 and may be referred to as a second portion of the interlock release mechanism 56.

A result of this is that the user can make small displacement adjustments to the axial position of the shield 18 whilst locating an injection site before applying an increased level of force to activate the insertion and delivery phases. The range of the small displacements is limited by the increased force required to activate the insertion which the user would feel as a defined resistance to the depression of the shield 18.

FIG. 9c shows the activation phase of the auto-injection. The activation is triggered by the user depressing the injection device 10 into the injection site which pushes the shield 18 rearwards relative the outer casing 12. The rearwards movement of the shield 18 causes the track 70 to axially translate relative to the protrusion 72 until it contacts the release surface 76 of the third portion 84 of the track 70.

The release surface 76 is obliquely inclined relative to the longitudinal axis such that the axial translation induces a relative rotation between the shield 18 and barrel housing 52. The corresponding portion of the interlock 54 includes a short steep forwards ramp which restricts the rotation and requires a user to provide a predetermined amount of axial force to overcome. The forwards ramped portion causes a rearward movement of the syringe carrier 26 relative to the housing. The rearward movement is resisted by the insertion spring which is urging the syringe carrier 26 forward via the abutment between the driving assembly and syringe carrier 26 via the barrel 20. Thus, the ramped portion and the rearward movement provide a resistance to the axial displacement of the shield 18 and an increased force required from the user. It will be appreciated that the steeper the ramp, the greater the force is required to overcome it.

With the increased depression of the shield 18, the syringe carrier stop 62 overcomes the ramped portion and slides off the syringe carrier housing stop 60. At this point, the drive assembly 32 is activated and moves the syringe carrier 26 forward under the driving force of the insertion actuator 48. This is described separately below.

It will be noted that the final section of the syringe carrier stop 62 includes a rearwards ramp which encourages the disengagement of the two stops and provides the final rotation of the syringe carrier to axially align the protrusion 72 with the park position.

The protrusion 72 travels in the track 70 until the syringe carrier abuts stop features (not shown) on the internal wall of the outer casing which coincides with the protrusion reaching the terminal end of the second leg, as shown in FIG. 9d. This limits the travel of the syringe carrier 26 and defines the limit of the insertion stroke. Once insertion is complete, the bung 28 can be driven down the barrel 20 to carry out the injection, which is described below.

After the injection is complete, the device can be withdrawn which results in the shield 18 being driven forwards under the force of the lock-out spring 64. As shown in FIG. 9e, this causes the protrusion 72 to move to the rear of the track 70 and hit the lock-out surface which coincides with the lock-out shield 18 engaging with a pair of lock-out tabs which extend from the outer casing 12.

It will be noticed that the activation phase of the track 70 may include a dog-leg portion defined in part by a shoulder 92 which lies along a length of the inner track. This mirrors the travel of the protrusion, with clearance, as it is rotated by the final portion of the stop 62. The final rotation of the syringe carrier places the protrusion 72 in axial alignment with the park position surface 78. Hence, once the protrusion 72 is in the delivery position, it only requires an axial translation of the shield 18 for the protrusion 72 to engage the park position surface 78.

The park position surface 78 is provided by a protuberance in perimeter wall of the track 70, but it will be appreciated that the lock-out surface could also be provided by a cut-out or notch in the perimeter wall of the track 70. Providing a notch rather a protuberant shoulder allows the lock-out throw of the shield to be longer.

Enabling the rotation of the syringe carrier 26 as per the described example allows the lock-out shield 18 to be held at a constant angular position relative to the housing so that there is no discernible rotation on a user's skin at the injection site. Hence, in some examples, the interlock portion of the syringe carrier 26 is rotated relative to the outer casing 12 (or syringe carrier housing 58) and the shield 18 by common amounts during the siting of the injection and the activation.

Figure 10:
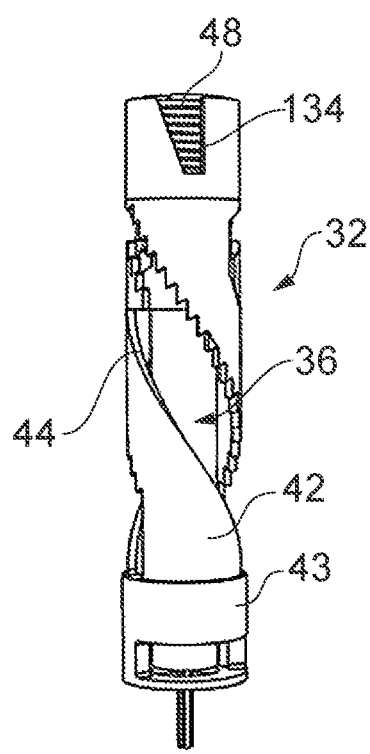
FIG. 10 show a driving assembly.
Figure 11A:
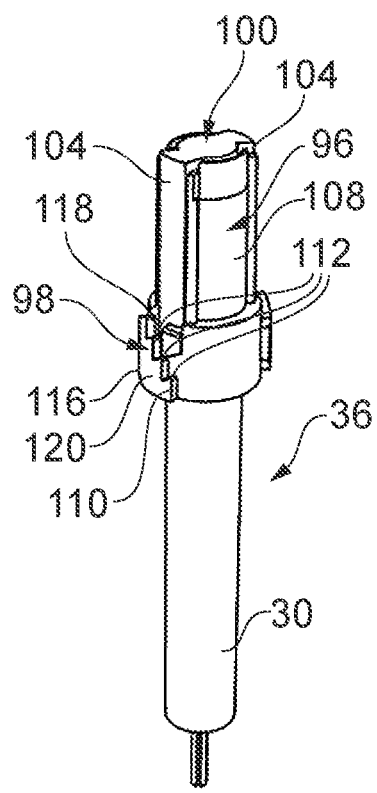
FIGS. 11a to 11c show some constituent parts of the driving assembly.
Figure 11B:
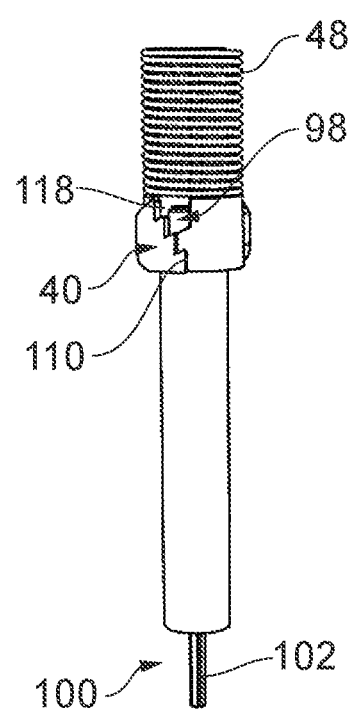
Figure 11C:
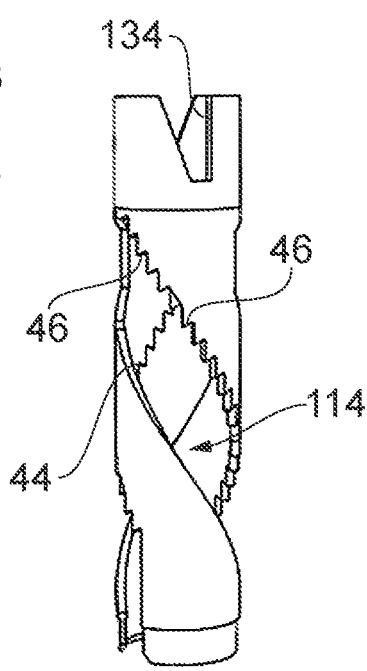

FIG. 10 shows the drive assembly 32 removed from the outer casing 12, with FIGS. 11a to 11c showing some of the constituent components within the drive assembly 32. Thus, there is shown a firing cartridge 36 in isolation in FIG. 11a and the firing cartridge 36 with a priming arrangement which, in this example, is an insertion actuator 48 in FIG. 11b. FIG. 11c shows a sleeve 42 in which the firing cartridge 36 and insertion actuator 48 may be located. FIG. 10 shows the parts assembled with an end cap 43 which terminates the sleeve 42 and provides an abutment surface for the distal end of the barrel 20 and/or the syringe carrier 26 to engage with.

The drive assembly 32 has a longitudinal axis which is co-axial with the longitudinal axis of the auto-injection apparatus 10.

The firing cartridge 36 is movable between a stowed (e.g. a pre-delivery position) and a delivery position in which a plunger 30 is in contact with or close proximity to the bung 28 so as to be correctly positioned for carrying out the injection. The drive assembly 32 includes a delivery actuator 38 and one or more components required to activate the delivery actuator 38 when located in the appropriate delivery position. The delivery actuator 38 may be in the form of a delivery spring. The delivery spring may be contained within a restraint prior to being activated, and released from the restraint once activated.

The firing cartridge 36 includes a proximal end and a distal end relative to the needle 14 and may include two more axial portions which are separable during use. Thus, the firing cartridge 36 may include a first part and a second part which define the proximal and distal ends. In the example shown in FIG. 10 et seq., the first part provides the plunger 30 which is passed through the barrel 20 to deliver the injection when in use. The second part is provided by the back portion 96 which encloses and restrains the delivery spring within the plunger 30. The delivery spring extends longitudinally within the housing and is compressed by the opposing internal surfaces of the plunger 30 and back portion 96. The plunger 30 and back portion 96 are axially detachable to allow the plunger 30 to be pushed forward relative to the spring housing when the delivery actuator 38 is activated.

Prior to activation the first part and second part of the firing cartridge 36 are detachably attached at a coupling. The coupling 98 may be provided by any suitable structure such as a latch or interlock, for example. The coupling 98 may be provided by a bayonet fitting. A firing mechanism may be included as part of the firing cartridge 36. The firing mechanism is configured to decouple the first and second parts of the firing cartridge 36 when triggered.

The firing mechanism may include a pressure responsive trigger which activates as the firing cartridge 36 approaches the bung 28. In the example shown in FIG. 10, the pressure responsive trigger is in the form of a firing pin 100. The firing pin 100 may extend forwards of the firing cartridge 36 and provide a point of first contact between the firing cartridge 36 and the syringe. The corresponding contact point of the syringe may be a surface of the bung 28. As shown, the surface of the bung 28 may be rearward facing surface. But the delivery actuator 38 may contact another part of the syringe or an adjacent structure which is sufficiently close to the syringe to reduce the distance between the plunger 30 and the bung 28 by the required amount.

The firing pin 100 may include or be in mechanical communication with the firing cartridge coupling 98 which acts to directly or indirectly couple the first and second parts of the firing cartridge 36 together in the pre-delivery configuration. As the firing pin 100 contacts the corresponding contact point of the syringe, it may move rearwards relative to the firing cartridge (which is moving forwards), thereby disengaging the interlock so that the delivery actuator 38 may be activated and drive the plunger 30 towards the syringe.

FIGS. 11a to 11c show an example of the firing cartridge 36 in which there is shown a firing pin 100, a delivery actuator 38 in the form of a delivery spring, a back portion 96 and a plunger 30.

The firing pin 100 includes an elongate pin member 102 that extends axially in use and may be co-axial with the longitudinal axis of the auto-injector. The firing pin 100 may be received within the central bore of the delivery spring and be T-shaped with a pin member 102 extending axially forwards from a back plate. The junction between the pin member 102 and the back plate may be at a mid-point of the latter.

A pair of arms 104 extend axially forwards from the back plate parallel to the pin 102 on diametrically opposite sides thereof. The free ends of the arms 104 form part of the firing cartridge 36 coupling, providing a key 118 which prevents decoupling. The pin member 102 of the firing pin 100 is an elongate shaft which passes through the back portion 96 and plunger 30 to protrude axially forwards of the plunger 30 to provide the trigger point for contact with the bung 28.

The plunger 30 may be cylindrical and have a closed proximal end and an open distal end which reveals a hollow interior. The hollow interior receives the pin member 102 and delivery spring. The closed end of the plunger 30 includes an aperture through which the pin member 102 passes to protrude axially forwards of the terminal end of the plunger 30 thereby providing the first point of contact for the firing cartridge in relation to the bung.

The back portion 96 provides a seat for the distal end of the delivery spring. The back portion 96 comprises a hollow main body in which the delivery spring can be seated. The seat may be provided at a terminal end of the hollow back portion 96. The combination of the back portion 96 and the plunger 30 provide for an enclosure in which the delivery actuator 38 can be located and restrained, prior to activation.

Figure 14:
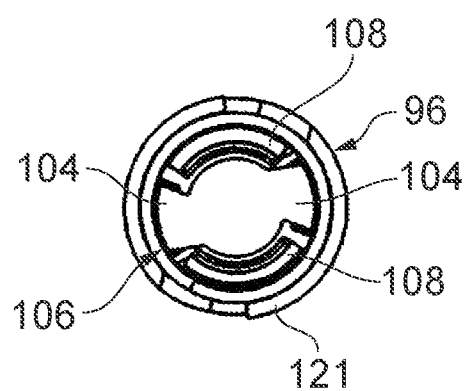
FIG. 14 shows a proximally inwards end view of the drive assembly.

The back portion 96 may include one or more of: firing pin engagement features 106; outer casing location features 108; a cartridge coupling 98; and guide member 120. Thus, as shown in FIG. 11a and FIG. 14 the back portion 96 includes a pair of diametrically opposed channels on an exterior surface thereof for receiving the arms 104 of the firing pin 100. In the example shown, the channels are defined by axially extending radial flanges and terminate at the bayonet fitting which provide the firing cartridge coupling.

The outer casing location features 108 include a further pair of channels which extend axially down the exterior of the back portion 96. The channels are arcuate in section and receive corresponding arcuate location flanges 122 which extend from an inner distal surface of the outer casing end cap 121. This is described in more detail below.

The distal end wall of the back portion 96 includes an aperture for receiving the firing pin 100 such that it can pass through the full length of the firing cartridge 36.

Also located on the exterior of the back portion 96 are cartridge backstops 40. The cartridge backstops 40 may engage with corresponding features of the delivery assembly to prevent the firing cartridge 36, or more particularly, the back portion 96, moving rearwards once the interlock 54 has been separated.

The length of the firing cartridge 36, and in particular the combined length of the plunger 30 and back portion 96, will be determined, at least in part, by the dimensions of the spring in the primed and activated configurations and the required travel. As will be appreciated, the dimensions of the spring will be determined by the required properties for driving the plunger 30.

As described above, the firing cartridge 36 is movable between a stowed position and a delivery position. In the described example, this is achieved by moving the firing cartridge 36 axially forwards into a delivery position proximate to the syringe. Once the firing cartridge 36 is in, or close to being in, the delivery position, it is activated such that the delivery actuator 38 is driven forwards into the barrel 20 of the syringe. In order to achieve this, it is desirable to prevent or limit the backwards movement of the firing cartridge 36 back along the path it travelled from the pre-delivery position. The restriction of the backwards movement of the firing cartridge 36 may be achieved in numerous ways, one of which is to use a backstop.

The backstop may be any feature which is either located or locatable to the rear of a surface of a cartridge backstop and which obscures the return path of the firing cartridge 36. The backstop may, for example, include a ratchet formation which is slidable in a first direction and latches in an opposing second direction. Such a ratchet may be provided by one or more barbs or the like on the firing cartridge 36 or outer casing 12 for example. Alternatively, the backstop may be provided by axially opposing surfaces placed on the outer casing 12 or an intermediate structure, and the firing cartridge 36.

One option is to provide the cartridge backstops 40 with or on guide members 120 which extend from the exterior of the firing cartridge back portion 96 and are received in guide channels 114. The cartridge backstops 40 may take any form of feature which can engage with a corresponding feature on an axially opposing surface. The cartridge backstops 40 may include one or more steps, teeth, castellation, notch, protrusion 72 or high friction surface which are abutted against, interleaved or interlocked with an opposing corresponding formation.

In the example shown in FIG. 11a, the cartridge backstops 40 are provided by one or more teeth 110 which engage with corresponding portions on a static part of the auto-injector. Each tooth includes a distal rearward facing surface which provides a firing cartridge abutment surface 112 for engagement with a corresponding static backstop. As shown, the teeth 110 may be arranged in a linear cascade so as to provide a plurality of steps. Each of the abutment surfaces 112 may be ramped so as to be inclined to the normal of the longitudinal axis of the injection apparatus 10. To provide the ramp, each of the steps (or teeth) may be tapered such that a riser portion of the step and the abutment surfaces 112 are separated by an acute internal angle.

The opposing backstop surface which engages with the cartridge backstop 40 may be any suitable structure which can locate the back portion 96 in a stationary position relative to the syringe when the plunger 30 is driven into the barrel 20 against the bung 28 during the delivery phase. One option is to provide the backstop on the sleeve 42 which surrounds the firing cartridge 36, as described further below.

In order to provide reliable axial travel between the stowed position and the delivery position, the auto-injection apparatus 10 may include one or more guides to limit, direct and/or control the travel of the firing cartridge 36 within the outer casing 12. The one or more guides may include one or more guide surfaces 44 which engage with one or more opposing guide surface runners 116. The guides may be configured to rotate the firing cartridge 36 during the axial movement in addition to the axial travel.

The guide surface(s) 44 may be provided by a wall, ridge, rib, channel, track 70 or other suitable projection or depression location on or in the outer casing 12 or drive assembly 32.

FIGS. 10 and 11a show a sleeve 42 in which the firing cartridge 36 is coaxially nested. The sleeve 42 may provide a guide surface 44 in the form of the edge of a wall which bounds a channel. The sleeve 42 comprises a substantially elongate cylindrical structure which includes a distal end and a proximal end and is generally co-axial with the longitudinal axis of the auto-injection device. The sleeve 42 comprises a peripheral wall which defines a hollow interior in which the firing cartridge 36 resides.

The peripheral wall may include at least one channel 114 which extends axially from a distal end to a proximal end. The channel 114 may extend partway through the thickness of the peripheral wall so as to provide a longitudinal trough, or may be provided by lengthwise slots 134 in the sleeve 42 wall as can be seen FIGS. 10 and 11a. There may be a plurality of guide channels 114, each having a guide surface 44 for engagement with an opposing guide surface runner 116. The one or more guide channels 114 may extend axially, or circumferentially and axially to provide helical channels.

In the example shown in FIGS. 10 and 11, the sleeve 42 includes two helical channels which extend for the majority of the axial length of the sleeve 42 and terminate open ended at the proximal end. The helical guide channels 114 turn through a full revolution around the sleeve 42 but it will be appreciated that the number and geometry of the channels may be adjusted to suit a particular requirement.

The guide surface runners 116 are provided on the firing cartridge 36, typically on the back portion 96. In the example of FIGS. 11a and 11b, the aforementioned guide member 120 include guide surface runners 116 which engage with respective opposing guide surfaces 44 of the sleeve 42. The guide surface runners 116 comprise a proximal forward facing surface which is inclined so as to be obliquely arranged to the longitudinal axis. The angle of the guide runner surface corresponds to the guide surface 44 which is angled as a result of the helical profile.

The guide surface runners 116 and cartridge backstop 40 are provided on the same guide member 120 in the example of FIG. 11a, but it will be appreciated that this need not be the case, and the two elements may be provided at different locations. Further, it will be appreciated that there may be one or more guide surface runner 116 and cartridge backstop 40. In the example shown in FIG. 11a, there are a pair of guide surface runners 116 and cartridge backstops 40, each pair being diametrically opposed on either side of the back portion 96.

The helical channels in the sleeve 42 also provide a sleeve backstop 46 which can work in conjunction with the cartridge backstop 40. The sleeve backstop 46 is provided on the upper or distal edges of the helical channels so as to be axially separated from the guide surface 44 by the helical channel. Hence, each helical channel includes a linear distribution or cascade of steps or teeth which are shaped and sized to mate with the steps of the cartridge backstop 40. Thus, the helical channel may have a proximal edge which provides a guide surface 44, and a distal edge which is stepped along its length to provide an arrangement of sleeve backstops 46 for engaging with the firing cartridge 36.

The cartridge backstop 40 and sleeve backstop 46 may be arranged such that the two parts bind together when the firing cartridge 36 is urged rearwards during the delivery phase. In order to achieve this, the engaging faces of the backstops 40, 46 may be inclined slightly so as to impart a relative rotation between the firing cartridge 36 and sleeve 42 so as to push the two parts together.

This can be seen in FIGS. 10 and 11b, where each step on the sleeve backstop 46 includes a distal forward facing surface which provides an abutment surface for engaging with the cartridge backstop 40, and the abutment surface is inclined to the normal of the longitudinal axis of the injection apparatus 10 to provide a slide. The angle of inclination matches the cartridge backstop 40 steps. The angles are such that the backstops bind together when an axially rearward force is applied.

In use, the firing cartridge 36 is located within the sleeve 42 with the guide member 120s located within the helical channels. In this configuration, the guide surface runner 116s are located on the guide surface 44s and ready to move forwards.

The continuous distribution of sleeve backstops 46 on the upper edge of the helical channel provides a backstop 46 for each portion of the guide surface 44. Hence, the firing cartridge 36 can travel forwards within the sleeve 42 by an indeterminate amount before being moved rearwards by the delivery actuator 38 and aligning with a set of backstops 46. This is advantageous as it allows for numerous different fill levels to be accommodated. Where the alignment is out, the sloped abutment faces induce a binding rotation to back portion 96 to ensure that the back stops bind.

Hence, the guide surface 44 provides axial alignment between the sleeve backstop 46 and the cartridge backstop 40 during movement of the firing cartridge 36 from the stowed position to the delivery position.

It will be appreciated that it may not be necessary to provide a continuous distribution of backstops for the full length of the helical channel. For example, the backstops may only be provided over a range as determined by the possible fill levels which will be accommodated.

Returning to FIGS. 11a to 11c, the coupling 98 between the plunger 30 and back portion 96 is provided by a bayonet fitting. The bayonet fitting may be a push and twist attachment in which the plunger 30 and back portion 96 axially mate prior being twisted relative to each other. Hence, one or the other of the plunger 30 and spring housing may include an axial channel and a circumferential channel with a corresponding projection provided on the other of the plunger 30 and back portion 96. In the example shown, the back portion 96 includes the channel, and the plunger 30 includes the projections.

It will be appreciated that the axial channel may have a circumferential component and the circumferential channel may have an axial component. The circumferential part of the channel may include an axially inclined circumferential seat.

The firing pin key(s) 118 located at the end of the firing pin arms 104 may be located within the axial part of the channel so as to at least partially block the circumferential path and prevent the relative rotation of the back portion 96 and plunger 30, thereby locking the coupling 98. The movement of the firing pin 100 rearwards with the contact with the bung 28, results in the keys 118 moving rearwards and the plunger 30 and back portion 96 relatively rotating so as to become separated.

The driving assembly may include a priming arrangement which moves the firing cartridge 36 axially forwards from the stowed position to the rearwards position. The primary arrangement may include a priming actuator which is located at the distal end of the drive assembly 32 and acts to drive the drive assembly 32 and/or firing cartridge 36 axially forwards during firing.

As can be seen by the example shown in FIGS. 10 and 14, the priming actuator is provided by a compression spring. The spring is located around the back portion 96 of the firing cartridge 36 and is received on a seat provided by an axially rearward facing seat of the back portion 96. The spring is located within the sleeve 42.

Figure 12A:
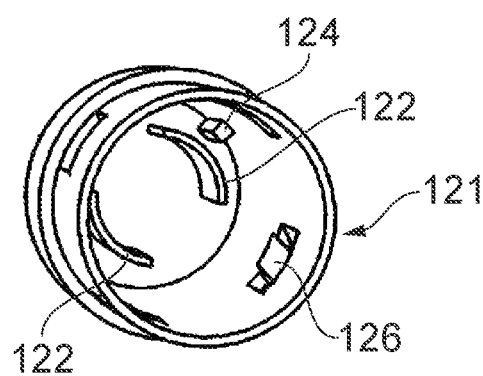
FIGS. 12a and 12b show a portion of the outer casing which partially houses the drive assembly.
Figure 12B:
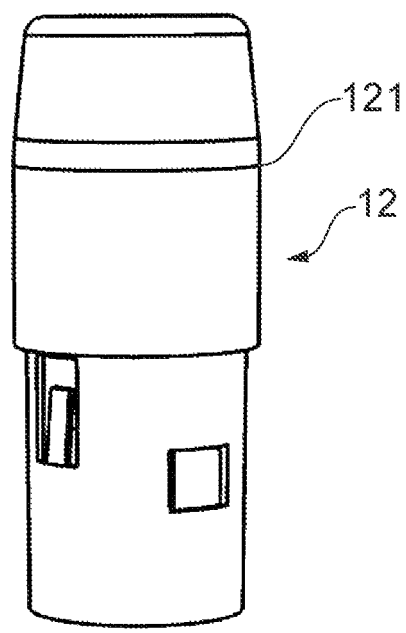
Figure 13:
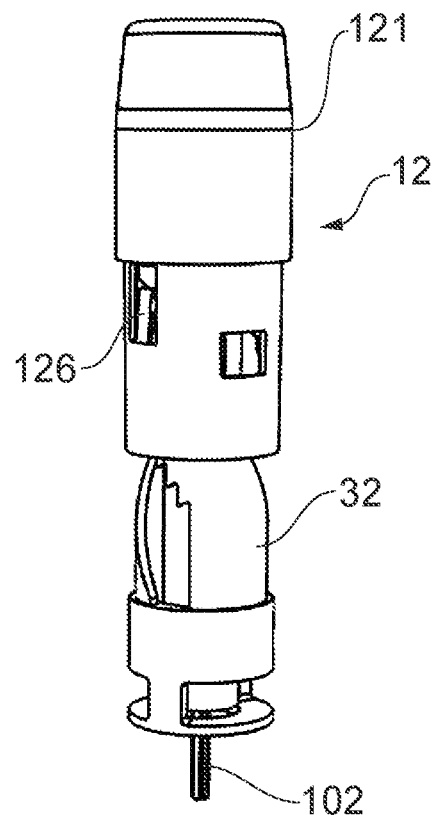
FIG. 13 show the drive assembly of FIG. 10 in the portion of outer casing shown in FIGS. 12a and 12b.

FIGS. 12a and 12b show a first or distal portion of the outer casing 12. The distal portion may be attached to one or more proximal portions to provide the outer casing 12. The distal portion includes an end wall and a peripheral wall which define an internal cavity in which the drive assembly 32 is located and may be referred to as the outer casing end cap 121. The end cap 121 includes a pair of arcuate flanges 122 which extend from the internal surface of the end wall and provide location features for the drive assembly 32. As can be seen in FIG. 14, the arcuate flanges 122 are received within corresponding channels provided by the back portion 96, radially inwards of the insertion/priming spring.

The end cap 121 may also include one or more anti-rotation engagements 124 in the form of projections which are received within slots 134 provided in the distal end of the sleeve 42. As shown, the projections may be elongate ribs which axially engage with the sleeve slots 134.

The terminal end of the anti-rotation engagements 124 are positioned such that the sleeve 42 can undergo a predetermined forwards axial displacement before passing the engagements and being allowed to rotate. Once this occurs, the projections provide a distal stop for the sleeve 42 which engages with the distal end of the sleeve 42 and prevents the sleeve 42 moving rearwards. This is described in more detail below.

The drive assembly 32 may be retained by a latch 126 in the end cap 121 prior to the end cap 121 being attached to the main body of the outer casing 12. A biasing member may be between the end cap 121 and the drive assembly 32, the biasing member urging the drive assembly 32 out of the end cap 121 and against the latch.

The biasing member may be the priming actuator or the insertion actuator 48. As noted above, the priming actuator and insertion actuator 48 may be provided by the same actuator/spring.

The injection device may also include a latch release mechanism 128 for disengaging the latch upon the attachment of the end cap 121 and the main body during assembly of the outer casing 12 such that the biasing member urges the drive assembly 32 forwards beyond the latch 126 once the latch has been disengaged.

FIGS. 12a and 12b show a latch 126 which engages with a feature of the drive assembly 32 so as to retain it within the end cap 121 prior to assembly. Prior to assembly, the insertion spring is in a relaxed state and extends aft of the end of the firing cartridge 36. Inserting the drive assembly 32 into the end cap 121 compresses the insertion spring so as to bias the drive assembly 32 out of the end cap 121.

The drive assembly 32 is inserted until the latch 126 engages with a latch stop 128 on the drive assembly 32.

The latch 126 may be any suitable releasable attachment which can accept the drive assembly 32 when inserted, before being disconnected or decoupled when the main body of the outer casing 12 is assembled with the end cap 121. As shown in FIGS. 12a and 12b, the latch 126 may be a resilient deformable tab which extends into the interior of the end cap 121 in a rest position, and which is deflected upon insertion of the drive assembly 32 prior to engagement with the latch stop 128.

Figure 15A:
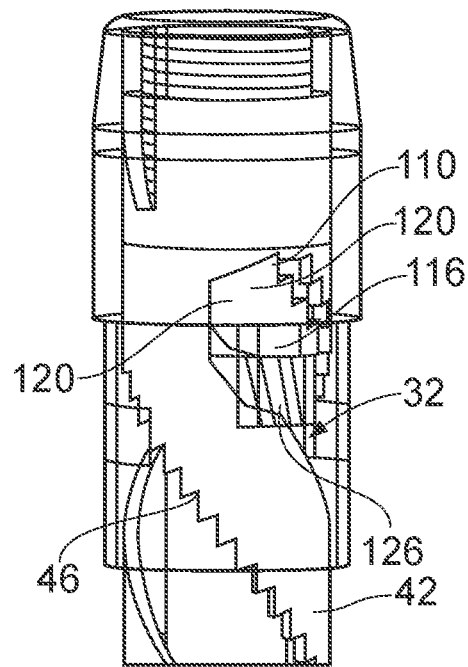
FIGS. 15a and 15b show a side view and section of the drive assembly and outer casing end cap prior to assembly of the injection device.
Figure 15B:
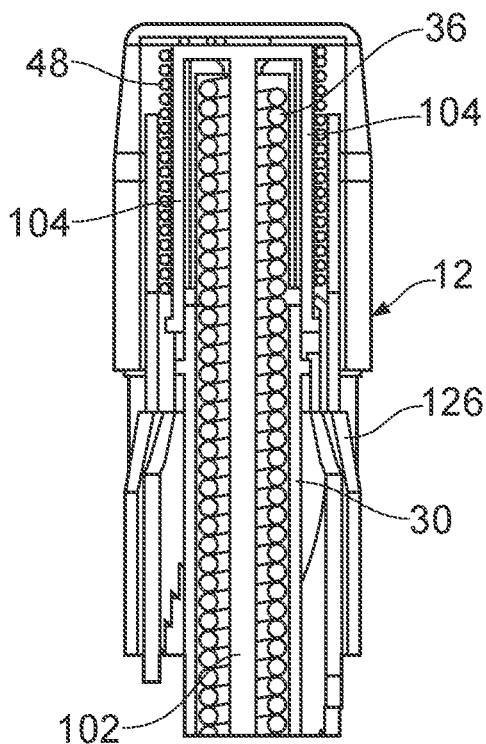
Figure 16A:
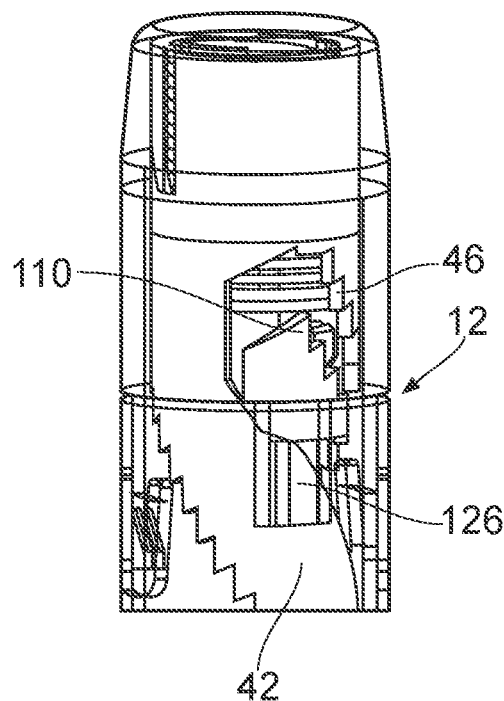
FIGS. 16a and 16b show the same as FIGS. 15a and 15b but with the injection device assembled.
Figure 16B:
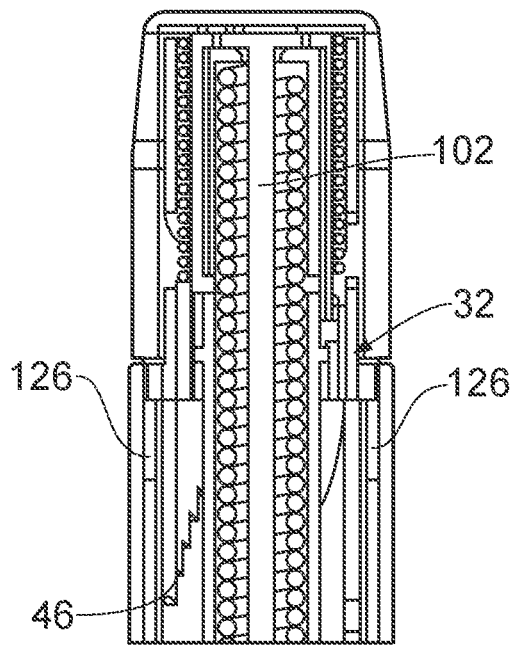

As best seen in FIGS. 15a, 15b and 16a, 16b, the latch 126 engages with an underside (or proximal surface) of the firing cartridge 36. In particular, the latch engages with the underside of the back portion guide members 120 which provide the guide surface runners 116 (FIG. 15b). The main body of the outer casing 12 is preloaded with the syringe carrier 26 before being offered up to the end cap 121 and drive assembly 32. The distal end of the main body accepts the proximal end of the drive assembly 32 which is inserted until it contacts the distal end of the barrel 20. At this point, the two parts of the outer casing 12 are not attached. Bringing the end cap 121 and main body further together urges the sleeve 42 rearwards into the end cap 121 until the walls of the sleeve 42 displace the latch and disengage it from the firing cartridge 36.

Upon disengagement, one or more catches 130 (best seen in FIGS. 6a, 6b) engage between the proximal portion of the outer casing 12 and the end cap 121 to attach the two components together such that they cannot axially separate when released. At this point, the insertion actuator 48 is pushing forwards on the syringe driver via the drive assembly 32 and barrel 20 with the interlock 54 preventing the forward movement. This state remains until the interlock 54 is disengaged, as described above.

It will be appreciated that the release may occur at any point during the assembly, and does not need to be at the moment where the end cap 121 and main body become fixedly attached.

Figure 17A:
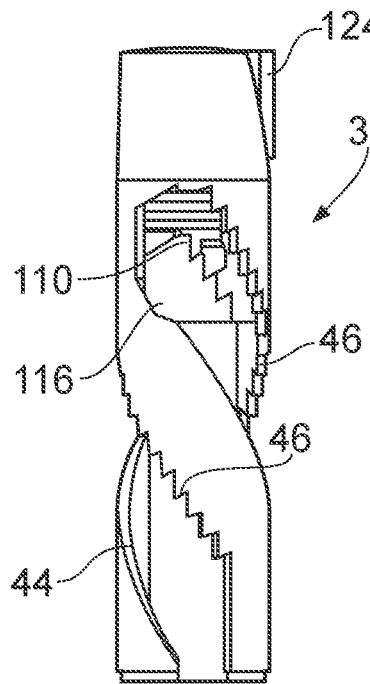
FIGS. 17a to 17e show the operational phases of the drive assembly.
Figure 17B:
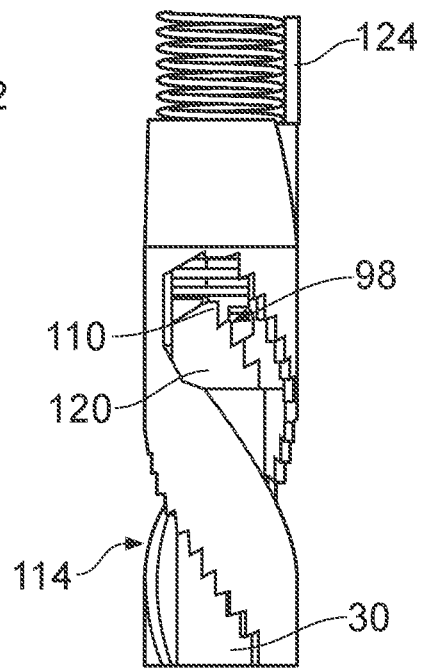
Figure 17C:
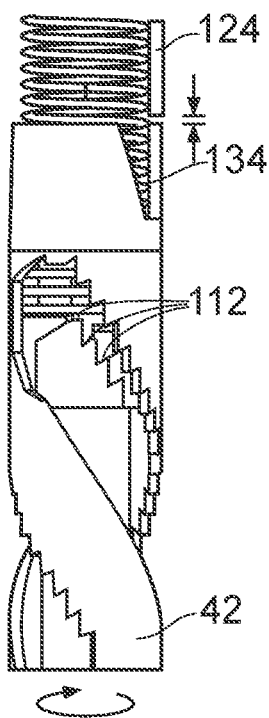
Figure 17D:
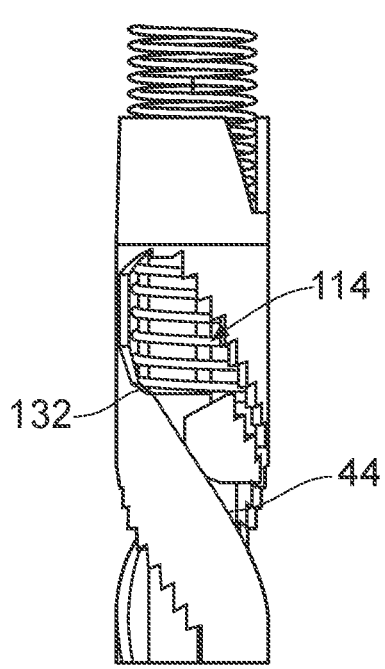
Figure 17E:
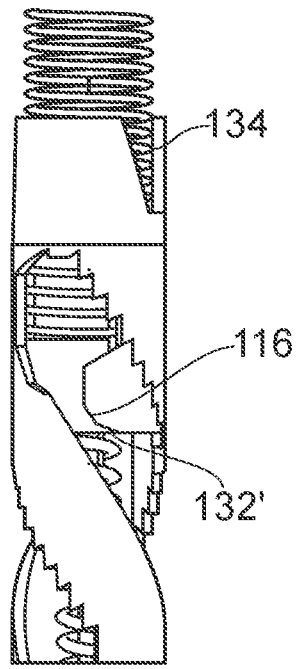

FIGS. 17a to 17e show the drive assembly 32 firing sequence in which the assembly progresses from the assembled state (FIG. 17a) through to activation and insertion (FIG. 17b), sleeve rotation and lock-out (FIG. 17c), deployment of the firing cartridge 36 into the delivery position (FIG. 17d) and delivery in which the backstops are engaged (FIG. 17e).

In FIG. 17a, the guide surface runner 116 engages with a distal end of the sleeve 42 guide runner. The guide surface 44 includes a lead-in 132 section which has a shallower angle than that of the main guide surface 44. The shallower angle is matched by a downstream angle 132' of the guide surface runner 116. Thus, the guide member 120 may comprise at least two angles of guide surface runner in which a first, shallower, angle 132' precedes a second steeper angle. Similarly, the guide surface 44 may have at least two angled portions, in which a first portion 132 is shallower than the second portion, the first portion being upstream of the second portion in relation to the direction of travel of the guide surface runner 116.

The shallower portions of the guide surface 44 and guide surface runner 116 are in abutment once the device is assembled, prior to activation. As such, the force of the insertion spring which urges the firing cartridge 36 forward, may pass through the firing cartridge 36 into the sleeve 42, before being transferred to the syringe carrier 26 and outer casing 12 via the barrel 20 which abuts the proximal end of the sleeve 42, and the interlock 54 between the syringe carrier 26 and syringe carrier housing 58. It will be appreciated that the relative angles of the guide surface portions may be altered to suit a particular performance requirement.

Once the device is activated by releasing the interlock 54, the drive assembly 32 moves forwards from the assembled position, thereby pushing the needle 14 forwards for insertion via the syringe carrier 26, as shown in FIG. 17b. This continues until the sleeve 42 is free from the anti-rotation engagements 124 which limit the travel of the sleeve 42 to the axial direction. Once clear of the anti-rotation engagements, the sleeve 42 is free to rotate as demonstrated in FIG. 17c. The guide surface 44 and guide surface runner 116 are such that a rotation is induced on the sleeve 42 by the axial force provided by the firing cartridge 36. The anti-rotation engagements 124 are shown in FIG. 12a in the form of elongate ribs and received within the anti-rotation slots 134 which extend axially forwards from an open end in the distal end of the sleeve 42.

The rotation of the sleeve 42 shifts the angular position of the anti-rotation engagements 124 relative to the sleeve 42 anti-rotation slot 134 such that they can abut the distal edge of the sleeve 42 and provide a distal stop. Thus, the sleeve 42 cannot move rearwards during the injection phase. It will be appreciated that the anti-rotation engagements 124 and distal stop are advantageously carried out by a common member in this instance, but this need not be the case and these separate functions may be carried out by separate features, where appropriate.

Once the guide surface runner 116 clears the shoulder which separates the first and second portions between the angled portions of the guide surface 44, the firing cartridge 36 can be driven forwards within the sleeve 42 until the firing pin 100 contacts the rear surface of the bung 28 (FIG. 17d). This results in the firing cartridge 36 decoupling and the plunger 30 expanding against the bung 28 and driving the back portion 96 rearwards to engage the back stops (FIG. 17e) from where the delivery is carried out.

Figure 18A:
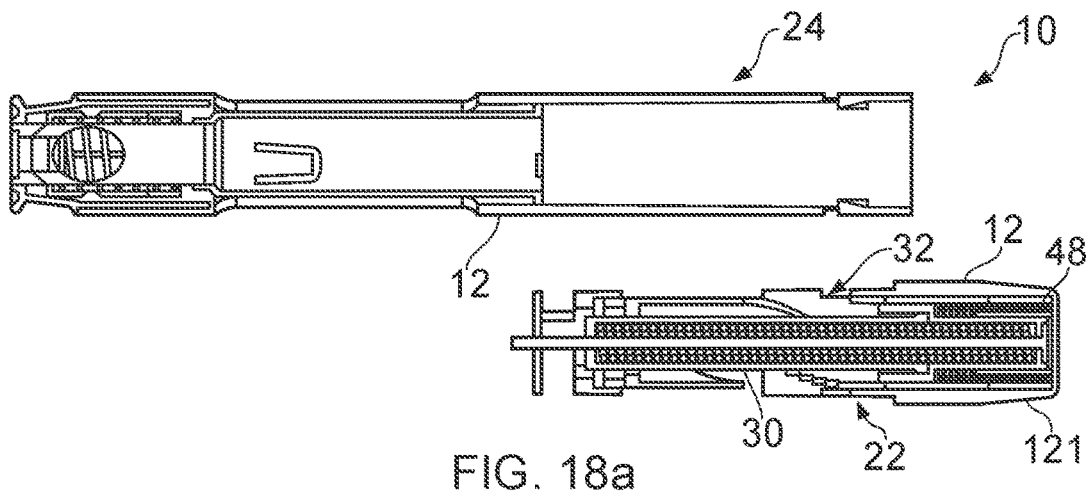
FIGS. 18a to 18i show longitudinal section views of an injection device through the operational phases; and, FIGS. 19a to 19e show side views of an alternative drive assembly and the associated operational states.
Figure 18B:
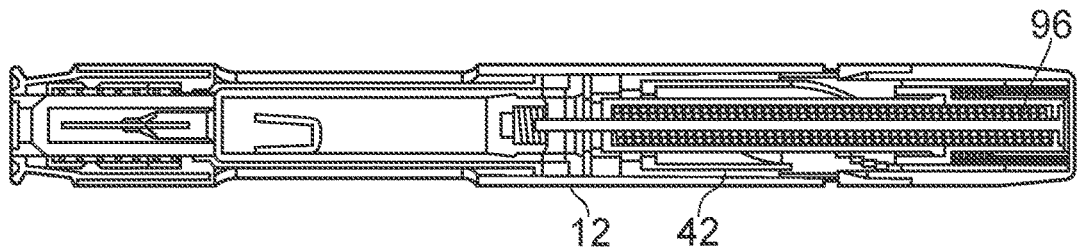
Figure 18C:
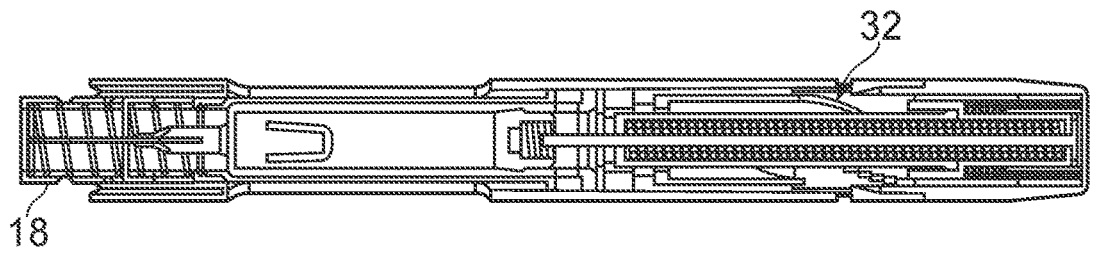
Figure 18D:
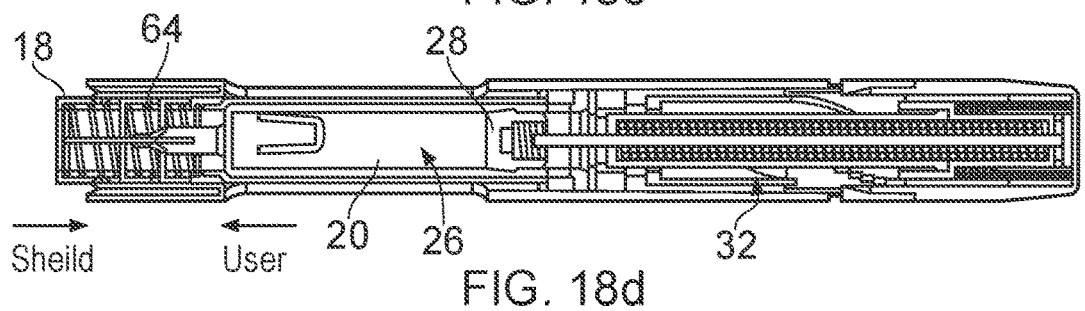
Figure 18E:
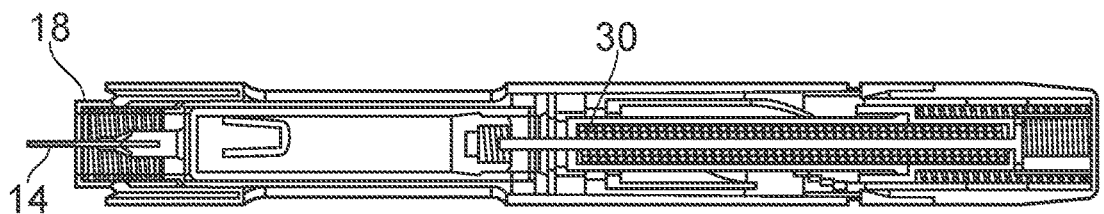
Figure 18F:
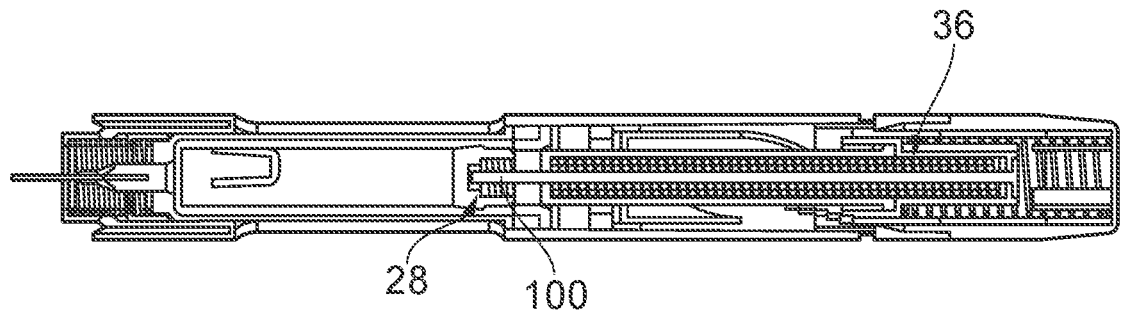
Figure 18G:
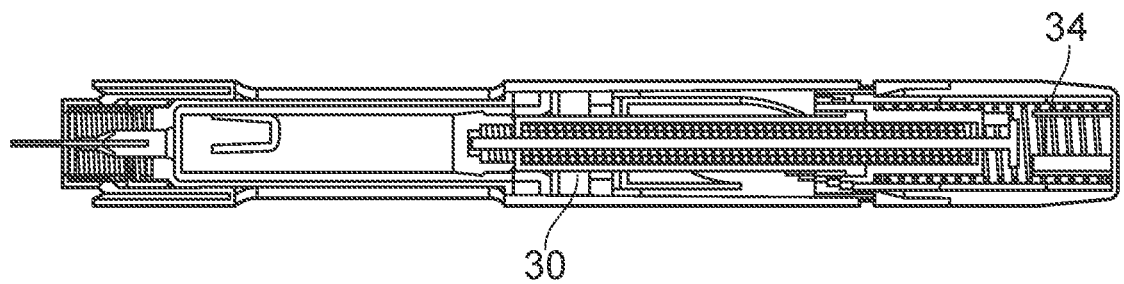
Figure 18H:
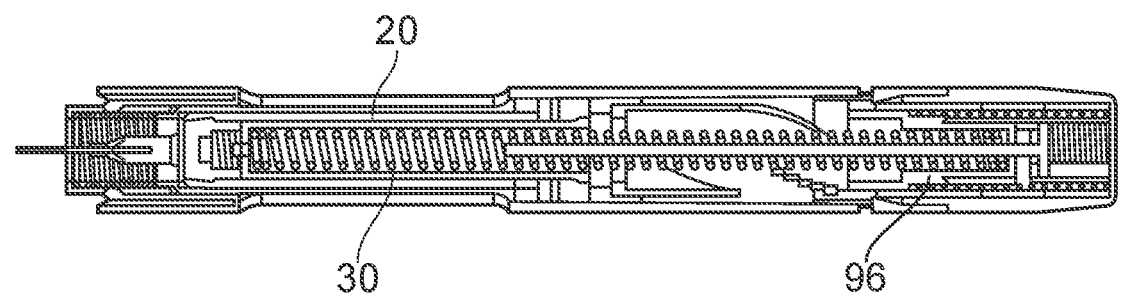
Figure 18I:
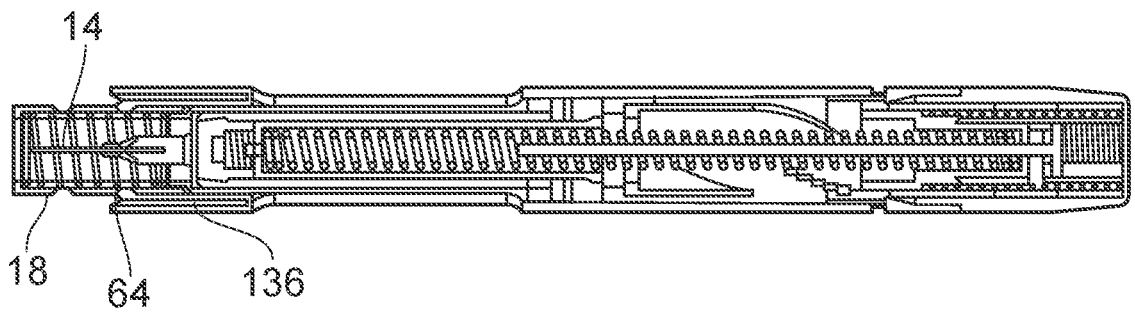

FIGS. 18a to 18i show sections of one example auto-injector which incorporates many of the features described above in a single device. FIG. 18a shows the front and rear sub-assemblies in the respective parts of the outer casing 12 prior to assembly. Thus, the end cap 121 has the drive assembly 32 mounted therein and latched in place, and the proximal end of the outer casing 12 has the syringe carrier 26 loaded therein. FIG. 18b shows the device assembled, with the sleeve 42 pushed rearwards by the barrel and/or syringe carrier to disengage the drive assembly retaining latch (not shown). FIG. 18c shows the cap 16 removed and the shield 18 deployed ready for the location of an injection site. FIG. 18d shows the beginning of the activation stroke in which the shield 18 is depressed into the outer casing 12 by the user application pressure on the outer casing 12 into the injection site. FIG. 18e shows the activation of the device and the insertion of the needle 14 into the injection site. At this point interlock 54 is released by the interlock release mechanism 56 (not shown) and the syringe carrier 26 and drive assembly 32 are thrust forwards by the insertion spring, thereby inserting the needle 14 into the injection site. FIG. 18f corresponds to the firing cartridge 36 being moved from the stowed position towards the bung 28 until the firing pin 100 contacts the bung 28 at FIG. 18g. This pushes the back plate, arms 104 and keys 118 of the firing pin 100 rearwards to decouple the plunger 30 and back portion 96 such that the cartridge backstop 40 is forced rearwards into the sleeve backstop. The delivery spring is then released to expand and drive the bung 28 through the barrel 20 and expel the substance from the needle 14 and into the injection site (FIG. 18h). FIG. 18i shows the device withdrawn from the injection site and the shield 18 deployed and locked by the lock-out arms 136 which reside in the proximal end of the outer casing.

FIGS. 19a to 19e show an alternative guide assembly for deploying a firing cartridge 36' which may be provided for use in the injection apparatus 10. As with the previously described drive assembly 32, a drive assembly 32' may be housed in an outer casing (not shown) rearwards of the syringe carrier (not shown) and comprise the firing cartridge 36' and a sleeve 42' in which the firing cartridge 36' is located. The firing cartridge 36' is configured to move forwards between a stowed position and a delivery position and may comprise: a drive actuator; a guide surface runner 116'; and, a cartridge backstop 40'.

The sleeve 42' comprises one or more rearward facing guide surfaces 44' for engagement with the guide surface runner 116' so as to direct the forward movement of the firing cartridge 36' from the stowed position to the delivery position. The sleeve 42' also comprises a sleeve backstop 46' which engages the cartridge backstop 40' to prevent rearwards movement of a plunger 30' when the firing cartridge 36' is in the delivery position.

The firing cartridge 36' and sleeve 42' are similar in some respects to those of the previously described examples. The sleeve 42' is provided by a generally elongate cylindrical wall in which the firing cartridge 36' resides and may comprise a channel 114' having opposing first and second edges as shown. The first edge is a guide edge 136' comprising the guide surface 44', and the second edge is a backstop edge 138' comprising a plurality of the sleeve backstops 46' distributed along a length thereof.

As shown, the channel 114' may be provided by a longitudinal slot in the wall of the sleeve 42'. It will be appreciated that there may be a plurality of channels 114' and these may be uniformly distributed around the sleeve 42'. The depicted example includes two diametrically opposed channels (only one of which can be seen).

The backstop edge 138' and guide edge 136' may be provided with a distribution of guide features which provide rearward guide surfaces 44'. The guide features may be provided by projections (or depressions) arranged along the lengths of the respective edge to provide a periodically undulating or stepped profile. Exemplary guide features may include spurs, teeth, castellations or pegs, for example. In the example of FIG. 19a, the guide edge 136' includes a linear array of guide edge teeth 140', and the backstop edge 138' includes a linear array of backstop teeth 142'. The teeth 140', 142' are arranged along the length of the respective edges for the extent necessary to provide a guide member 120' with the required travel to move the firing cartridge 36' from the stowed position to the delivery position.

The rearward facing surfaces provided by the guide features act as descending guide surfaces 44'. Thus, each of the backstop teeth 142' and guide edge teeth 140' each include a rearward facing descending guide surface 44'.

The firing cartridge 36' includes a guide member 120' which is received in the guide channel and includes a guide edge surface runners 116' for engaging with the descending guide surfaces 44' of the guide edge 136', and a backstop guide surface runners 116" for engaging with the descending guide surfaces 44' of the backstop edge 138'. The example shows a plurality of guide edge surface runners and backstop guide surface runners 116' but it will be appreciated that other examples may include only one of each.

The guide surface runners 116' of the guide member 120' are provided by guide member teeth 136' which may correspond in size and shape to the guide edge teeth and backstop teeth 138' so that they can interengage with each other.

The guide member 120' has an axial length and a width which extends across the width of the guide channel 114'. The lateral dimension of the guide member 120' is such that the guide member teeth may circumferentially overlap the teeth of the guide edge 136' and backstop edge 138'. This restricts the axial movement of the guide member 120' such that it cannot freely pass axially down the channel 114' without the teeth engaging each other on at least one side or the other. That is, the lateral extent of the guide member 120' measured between the peaks of the guide member teeth is greater than the separation of the peaks of the teeth of the guide edge 136' and backstop edge 138'. However, the overall lateral dimension of the guide member 120' is less than the trough to trough separation of the backstop edge 138' and guide edge 136' such that the guide member 120' can traverse the channel 114' by interleaving the teeth of the guide member 120' and respective edges on one side or the other.

In order for the guide member 120' to pass axially down the channel, the guide member 120' must oscillate laterally between the guide edge 136' and the backstop edge 138' as the firing cartridge 36' moves forward from the stowed position to the delivery position.

The guide member 120' may also include a cartridge backstop 40' having a rearward facing surface which engages with a forward facing surface of the backstop edge 138'. The cartridge backstop 40' is provided by the rearward facing surface of the backstop guide surface runner teeth 116'. The guide edge 136' additionally comprises a lead-on guide surface 47' which is arranged to direct the cartridge backstop 40' towards the sleeve backstop 46' upon rearwards movement of the guide member 120' within the channel.

The teeth of the guide edge 136' and backstop edge 138' may have different profiles to each other when viewed from radially inwards direction. The different profiles aid the back-locking functionality in which the cartridge backstop 40' and sleeve backstop 46' engage upon rearward movement of the guide member 120'.

As can be seen, the backstop edge teeth may be tapered such that the backstop surface and guide surface 44' are separated by an acute internal angle. The tapered teeth provide a spur or barb-like profile in which individual teeth point forwards creating a tapered re-entrant slot in the backstop edge 138'. The tapered slot receives a cartridge backstop 40' tooth upon rearward movement. More particularly, the backstop teeth each include a backstop descending surface 44' and a backstop surface. The backstop descending surface faces into the channel and rearwards. The backstop surface faces forwards and away from the channel. To describe it another way, the backstop edge 138' may comprise an array of forward facing barbs which trap the cartridge backstop 40' upon rearward movement of the guide member 120'.

The backstop surfaces may be inclined to the normal of the longitudinal axis by an angle alpha. Alpha may be between zero degrees and forty-five degrees. The backstop descending surface may be inclined at an angle beta. Beta may be between forty-five degrees and seventy degrees. The internal acute angle of the teeth may be between twenty degrees and sixty degrees.

The backstop descending surface and the lead-on surface of the guide edge 136' may be anti-parallel in that the descending surface and lead-on surface face rearwards and forwards respectively by similar but opposing angles to the longitudinal axis of the channel. Providing anti-parallel guide surfaces minimises the separation between the two edges which is required for the guide member 120' to laterally oscillate as it moves forward under the force of the priming actuator.

The guide edge teeth 140' comprise rearwards facing descending surfaces 44' and forwards facing lead-on surfaces 47', both of which face into the channel. The guide edge teeth 140' point generally rearwards by virtue of the descending guide surface 44' being shorter in length than the lead-on surface 47'. The angle of the descending guide surface 47' is oblique to the normal of the axis of the channel and may be between twenty and seventy degrees thereto. The internal angle of the guide edge 136' teeth are greater than that of the backstop edge 138' and may be obtuse, ranging from sixty-five degrees and one hundred and forty degrees. The larger internal tooth angles provide the saw tooth profile of the guide surface edge with a less severe profile than that of the backstop edge 138'. In particular, the guide surface edge has no re-entrant features which can entrap the guide member teeth during rearwards of forwards movement. Thus, the guide edge teeth 140' comprise two guide surfaces, whereas the backstop edge 138' provides a guide surface 44 and the backstop surface which entraps the cartridge backstop 40' upon rearward movement.

It will be appreciated that the guide edge teeth 140' and backstop edge teeth 140' are axially offset from one another to allow the rearwards engagement of the backstops when directed off the lead-on surface 47', but this need not be the case. The pitch and peak to trough of the backstop edge 138' teeth and guide edge 136' teeth may be the same but this is not necessary.

The proximal edge of the guide member 120' is angled to provide the rotation of the sleeve 42' relative to the outer casing and anti-rotation feature 124 in the end cap 121' once released following insertion, as described above in connection with FIG. 17c.

FIGS. 19a to 19e show the operation of the alternative arrangement in progressive stages. FIG. 19a shows the guide member 120' being urged axially forwards by insertion sprig (not shown) and rotating the sleeve 42' so that it is axially locked underneath the distal backstop/anti-rotation feature 124 (not shown). The sliding motion provided between the guide member 120' and the lead-in slope of the channel urge the guide member 120' laterally towards the backstop edge 138' until the guide member backstop teeth and the backstop edge 138' teeth interleaf with each other. The lateral movement continues until the guide edge teeth 140' and guide surface runners 116' are angularly displaced so as to be parted circumferentially and thus axially unrestricted on the guide edge side of the guide member 120' (FIG. 19b). At this point, the forwards force induced by the priming actuator causes the guide member 120 to slide axially forwards and laterally towards the guide edge via the sliding contact between the backstop descending surface 44' and the backstop guide runner surface 116' (FIG. 19c).

The lateral movement continues until the guide edge descending surface 44' contacts the corresponding runner surface 116' of the guide member 120', and the backstop surfaces become angularly displaced. In doing so, the lateral movement of the guide member 120' is reversed again and the guide member 120' is sent back towards the backstop edge 138'. Thus, the guide member 120' and firing cartridge 36' moves forward a discrete amount with each to and fro movement between the backstop edge 138' and guide edge 136'.

This oscillatory zig-zag travel pattern continues until the firing pin (not shown) contacts the reverse side of the syringe and the firing cartridge 36' decouples to activate the delivery actuator 38' and plunger 30' (FIG. 19d). Activation of the plunger 30' drives the cartridge backstop 40' rearwards such that the rearward facing lead-on surface 47" of the guide member 120' contacts the corresponding forward facing lead-on surface 47' of the guide edge 136' to direct the guide member 120' and cartridge backstop 40' laterally and rearwards towards the backstop surface of the backstop edge 138'. The respective angles of the cartridge backstop 40' surface and the backstop edge 138' surface translate the rearward force delivery actuator 38' into a further lateral movement which embeds the guide member 120' into the backstop edge 138' to prevent any further rearward movement (FIG. 19e).

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. An auto-injection apparatus for receiving a syringe, comprising:
an outer casing which encloses:
a syringe carrier configured to hold a barrel of the syringe and having a stowed position and a delivery position;
an interlock which extends between the syringe carrier and a syringe carrier housing which at least partially surrounds the syringe carrier, the interlock preventing the forward motion of the syringe carrier under the influence of an insertion actuator whilst in the stowed position;
an interlock release mechanism configured to release the interlock such that the insertion actuator drives the syringe carrier forward, the interlock release mechanism comprising:
a shield moveable relative to the syringe carrier and configured to provide a pressure activated trigger for the interlock release mechanism, and
a track and a protrusion, wherein one of the track and the protrusion is located on the syringe carrier, and the other of the track and protrusion is located on the shield; and
a removeable cap coupled to the shield and configured to prevent forward movement of the shield prior to use of the auto-injection apparatus,
wherein removal of the cap causes the shield to move forward relative to the outer casing and the syringe carrier into a deployed position, and wherein subsequent rearward movement of the shield into the outer casing and relative to the syringe carrier causes the protrusion to move within the track to activate the interlock release mechanism to release the insertion actuator to drive the syringe carrier forward.

2. An auto-injection apparatus according to claim 1, wherein the shield is slidably arranged between the outer casing and the syringe carrier.

3. An auto-injection apparatus according to claim 1, wherein at least a portion of the syringe carrier is received within the shield.

4. An auto-injection apparatus according to claim 1, wherein relative axial movement between the syringe carrier and the shield causes the protrusion to move within the track to rotate the syringe carrier.

5. An auto-injection apparatus according to claim 1, wherein the track comprises a priming portion, and wherein forward movement of the shield into the deployed position causes the projection to move within the priming portion of the track.

6. An auto-injection apparatus according to claim 5, wherein the priming portion comprises a terminal end and wherein further forward movement of the shield is prevented following removal of the cap when the projection abuts the terminal end.

7. An auto-injection apparatus according to claim 1, wherein the track comprises a release portion and wherein the subsequent rearward movement of the shield causes the protrusion to move within the release portion to disengage the interlock.

8. An auto-injection apparatus according to claim 7, wherein the forward movement of the shield causes the syringe carrier to rotate to align the protrusion with the release portion such that the protrusion enters the release portion on the subsequent rearward movement of the shield.

9. An auto-injection apparatus according to claim 7, wherein movement of the protrusion within the release portion causes rotation of the syringe carrier to disengage the interlock.

10. An auto-injection apparatus according to claim 4, wherein the track comprises an anti-rotation feature configured to allow a predetermined amount of axial movement of the shield without rotation of the syringe carrier when the shield is in the deployed position.

11. An auto-injection apparatus according to claim 10, wherein the anti-rotation feature comprises an axial surface of the track.

12. An auto-injection apparatus according to claim 1, further comprising a shield actuator configured to bias the shield forward relative to the outer casing.

13. An auto-injection apparatus according to claim 1, wherein the interlock includes a syringe carrier housing stop and a syringe carrier stop which axially abut one another to prevent forward motion of the syringe carrier.

14. An auto-injection apparatus as claimed in claim 1, further comprising an insertion actuator configured to move the syringe carrier forwards within the outer casing to insert a needle of the syringe into an injection site.

15. An auto-injection apparatus as claimed in claim 1, wherein the subsequent rearward movement of the shield into the outer casing and relative to the syringe carrier causes the protrusion to move within the track to activate the interlock release mechanism.

16. An auto-injection apparatus as claimed in claim 1, wherein the shield moves forward relative to the outer casing and the syringe carrier into the deployed position under the force of a shield actuator.

* * * * *